(12) United States Patent
Feldkamp et al.

(10) Patent No.: US 8,452,388 B2
(45) Date of Patent: May 28, 2013

(54) APPARATUS AND METHOD FOR ASSESSING VASCULAR HEALTH

(75) Inventors: Joseph R. Feldkamp, Appleton, WI (US); Jeffrey Robert Heller, Neenah, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 1051 days.

(21) Appl. No.: 12/464,640

(22) Filed: May 12, 2009

(65) Prior Publication Data

US 2010/0222696 A1 Sep. 2, 2010

Related U.S. Application Data

(60) Provisional application No. 61/156,269, filed on Feb. 27, 2009.

(51) Int. Cl.
*A61M 25/00* (2006.01)

(52) U.S. Cl.
USPC .......................................................... 600/547

(58) Field of Classification Search
USPC .......................................................... 600/547
See application file for complete search history.

(56) References Cited

U.S. PATENT DOCUMENTS

| | | |
|---|---|---|
| 4,114,606 A | 9/1978 | Seylar |
| 4,327,434 A | 4/1982 | Christopher |
| 4,433,693 A | 2/1984 | Hochstein |
| 4,531,526 A | 7/1985 | Genest |
| 4,688,580 A | 8/1987 | Ko et al. |
| 5,400,236 A | 3/1995 | Shimizu et al. |
| 5,489,847 A | 2/1996 | Nabeshima et al. |
| 5,722,997 A | 3/1998 | Nedungadi et al. |
| 5,830,131 A * | 11/1998 | Caro et al. ................... 600/300 |
| 5,848,213 A | 12/1998 | Rahn |
| 6,121,772 A | 9/2000 | Shih |
| 6,147,881 A | 11/2000 | Lau |
| 6,371,417 B1 | 4/2002 | Southon |
| 6,891,380 B2 | 5/2005 | Kesil et al. |

(Continued)

FOREIGN PATENT DOCUMENTS

| | | |
|---|---|---|
| EP | 1611841 A1 | 4/2006 |
| GB | 1320403 | 6/1970 |

OTHER PUBLICATIONS

International Search Report and Written Opinion PCTIB2010050169 dated Aug. 25, 2010.
English Abstract and Claims for EP 1264746.

(Continued)

*Primary Examiner* — Benjamin Packard
(74) *Attorney, Agent, or Firm* — Dority & Manning, P.A.

(57) ABSTRACT

Apparatus and methods for utilizing conductivity measurements to assess vascular health or to diagnose vascular conditions are disclosed. An exemplary method includes performing a first conductivity measurement of an extremity at a first elevation; elevating the extremity to a second elevation; performing a second conductivity measurement at the second elevation; and comparing the first conductivity measurement and the second conductivity measurement to determine a conductivity displacement $\Delta\sigma$. Another exemplary method includes maintaining a conductivity sensor adjacent to an individual for a period of time; performing a series of conductivity measurements; using the series of conductivity measurements to determine the transient behavior of the conductivity over the period of time; and using the transient behavior of the conductivity to assess the vascular health of the individual. A conductivity sensor and platform unit for performing conductivity measurements are also disclosed.

25 Claims, 9 Drawing Sheets

U.S. PATENT DOCUMENTS

| | | | |
|---|---|---|---|
| 6,916,968 | B2 | 7/2005 | Shapira et al. |
| 7,119,627 | B2 | 10/2006 | Sun |
| 7,501,622 | B2 | 3/2009 | Kawato |
| 7,561,000 | B2 | 7/2009 | Sauter et al. |
| 7,764,125 | B2 | 7/2010 | Dawe |
| 2004/0068205 | A1 | 4/2004 | Zogbi et al. |
| 2004/0116080 | A1 | 6/2004 | Chen et al. |
| 2005/0025797 | A1* | 2/2005 | Wang et al. ............ 424/422 |
| 2005/0090753 | A1 | 4/2005 | Goor et al. |
| 2005/0261797 | A1 | 11/2005 | Cyr et al. |
| 2006/0005845 | A1 | 1/2006 | Karr et al. |
| 2006/0033500 | A1 | 2/2006 | Wang et al. |
| 2006/0142658 | A1 | 6/2006 | Perkuhn et al. |
| 2006/0278019 | A1 | 12/2006 | Christian et al. |
| 2007/0069717 | A1 | 3/2007 | Cheung et al. |
| 2007/0108972 | A1 | 5/2007 | Blew et al. |
| 2008/0048786 | A1 | 2/2008 | Feldkamp et al. |
| 2008/0071168 | A1 | 3/2008 | Gauglitz et al. |
| 2008/0077042 | A1 | 3/2008 | Feldkamp et al. |
| 2008/0149366 | A1 | 6/2008 | Suzuki et al. |
| 2009/0079424 | A1 | 3/2009 | Tralshawala et al. |
| 2009/0224774 | A1 | 9/2009 | Smith |
| 2010/0219841 | A1 | 9/2010 | Feldkamp et al. |
| 2010/0222696 | A1 | 9/2010 | Feldkamp et al. |

OTHER PUBLICATIONS

Lynn W. Hart, Harvey W. Ko, James H. Meyer Jr., David P. Vasholz, and Richard I. Joseph, "A Noninvasive Electromagnetic Conductivity Sensor for Biomedical Applications", *IEEE Transactions on Biomedical Engineering*, vol. 35, No. 12, Dec. 1988.

Richard Reimann, "Nuclear Magnetic Resonance Field Discriminator Using Digital Techniques", *Journal of applied Mathematics and Physics*, vol. 18, 1967.

Michael D. Harpen, "Influence of Skin Depth on NMR Coil Impedance Part II", *Physics in Medicine and Biology*, vol. 33, No. 5, May 1988.

Daniel D. Roby, A Comparison of Two Noninvasive Techniques to Measure total Body Lipid in Live Birds, *The Auk*, vol. 108, Jul. 1991, pp. 509-518.

Robert Guardo, Guy Charron, Yves Goussard and Pierre Savard, "Contactless Measurement of Thoracic Conductivity Changes by Magnetic Induction", *Proceedings—19$^{th}$ International Conference—IEEE/EMBS*, Oct. 30-Nov. 2, 1997.

Michael A. Pfeifer, "Vascular Medicine of the Lower Extremities", *Medscape-American Diabetes Association's 59$^{th}$ Scientific Sessions*, Jun. 22, 1999.

Peter G. Arthur, Trevor J. Jones, Janice spruce, and Peter E. Hartmann, "Measuring Short-Term Rates of Milk Synthesis in Breast-Feeding Mothers", *Quarterly Journal of Experimental Physiology*, vol. 74, 1989, pp. 419-428.

Steven M. Frank, M.D., Edward J. Norris, M.D, Rose Christopherson, M.D., Ph.D., Charles Beattie, M.D., Ph.D., "Right-and Left-arm Blood Pressure Discrepancies in Vascular Surgery Patients", Anesthesiology, vol. 75, pp. 457-463, Sep. 1991.

Johannes Netz, Ewald Forner, Sabine Haagemann, "Contactless Impedance Measurement by Magnetic Induction—a Possible Method for Investigation of Brain Impedance", *Physiological Measurement*, vol. 14, pp. 463-471, Nov. 1993.

Michael D. Harpen, "Distributed Self-Capacitance of Magnetic Resonance Surface Coils", *Physics in Medicine and Biology*, vol. 33, No. 9, pp. 1007-1016, 1988.

Yi Liu, Charles Dang, Marisa Garcia, Hans Gregersen, and Ghassan S. Kassab, "Surrounding Tissues Affect the Passive Mechanics of the Vessel Wall: Theory and Experiment", *American Journal of Physiology: Heart Circulation Physiology*, vol. 293, H3290-H3300, Sep. 14, 2007.

Gail Grigsby Harrison, Ph.D. and Theodore B. Van Itallie, M.D., "Estimation of Body Composition: A New Approach Based on Electromagnetic Principles", *The American Jounal of Clinical Nutrition*, vol. 35, May 1982, pp. 1176-1179.

Ricardo Leiderman, Paul E. Barbone, Assad A. Oberai, Jeffrey C. Bamber, "Coupling Between Elastic Strain and Interstitial Fluid Flow: Ramifications For Poroelastic Imaging", *Institute of Physics Publishing*, vol. 51, 2006, pp. 6291-6313.

V.K. Jayasree, T.V. Sandhya, P. Radhakrishnan, "Non-invasive Studies on Age Related Parameters Using a Blood Volume Pulse Sensor", *Measurement Science Review*, vol. 8, Section 2, No. 4, 2008, pp. 82-86.

Jeroen G. Stinstra, Shibaji Shome, Bruce Hopenfeld and Rob S. Macleod, "Modeling the Passive Cardiac Electrical Conductivity During Ischemia", *Medical Biology Computing*, vol. 43, No. 6, pp. 776-782, Nov. 2005.

Richard D. Stoy, Kenneth R. Foster and Herman P. Schwan, "Dielectric Properties of Mammalian Tissues From 0.1 to 100 MHz: A Summary of Recent Data", Phys. Med. Biol., 1982, vol. 27. No. 4, 501-513.

Dieter Haemmerich, S. T. Staelin, J. Z. Tsai, S. Tungjitkusolmun, D. M. Mahvi and J. G. Webster, "In vivo Electrical Conductivity of Hepatic Tumours", *Physiological Measurement*, vol. 24, pp. 251-260 (2003).

H.S. Schnyders, Marie-Louise Saboungi, and J.E. Enderby, "Noninvasive Simultaneous Determination of Conductivity and Permeability", *Applied Physics Letters*, vol. 75, No. 20, pp. 3213-3215, Nov. 15, 1999.

Y.C. Fung, B.W. Zweifach, M. Integliatta, "Elastic Environment of the Capillary Bed", *Circulation Research*, vol. 19, p. 441, Aug. 1966.

D. Arnold and G.H. Meeten, "Frequency Effects in the Inductive Measurement of Electrical Conductivity", *Journal of Physics E: Scientific Instruments*, vol. 21, pp. 448-453, May 1888.

C. Gabriel, S. Gabriel and E. Corthout, "The Dielectric Properties of Biological Tissues" I. Literature Survey, *Phys. Med. Biol.*, vol. 41, pp. 2231-2248, Apr. 1996.

M. A. Esrick and D.A. McRae, "The Effect of Hyperthermia-Induced Tissue Conductivity Changes on Electrical Impedance Temperature Mapping", *Phys. Med. Biol.*, vol. 39, pp. 133-144, 1994.

John D. Jackson, *Classical Electrodynamics*, Magnetostatics, Faraday's Law, Quasi-Static Fields, John Wiley & Sons, 3$^{rd}$ Edition, pp. 180-181, 1999.

\* cited by examiner

APPARATUS AND METHOD FOR ASSESSING VASCULAR HEALTH

PRIORITY CLAIM

This application claims the benefit of priority of U.S. Provisional Patent Application Ser. No. 61/156,269 filed on Feb. 27, 2009 which is incorporated herein by reference for all purposes.

BACKGROUND

The use of conductivity measurements to analyze various characteristics of human tissue specimens has been shown to yield many practical advantages. For example, conductivity measurements may be used to distinguish diseased tissue from healthy tissue. Both conventional electrode and induction coil methods have been used to perform conductivity measurements of human tissue specimens.

Conventional electrodes for measuring conductivity of a human tissue typically apply an AC voltage to a specimen of interest. The current traveling through the specimen is measured and the conductivity is computed. In some cases, many electrodes are attached so that imaging of the specimen is made possible in circumstances where conductivity varies spatially through the specimen.

A disadvantage of conventional electrodes is that it requires direct electrical contact with the tissue specimen. This is particularly true for human tissue specimens because the stratum corneum layer of the epidermis impedes the flow of current through the specimen, leading to variable conductivity measurements. Conventional electrodes may also exhibit electrode polarization, resulting in inaccurate conductivity measurements.

Induction coil methods and devices for measuring conductivity have used a wide variety of induction coil designs including solenoids or simple loop type coils consisting of a few turns of wire. These coils may probe the human tissue specimen at depths allowing interferences from bone and/or internal organs that distort the conductivity measurement. Many of these devices also involve the use of expensive instrumentation to measure coil related parameters such as complex impedance and use circuitry that permits the induction coil to deviate from resonance as the coil is placed adjacent to a specimen, making measurement of conductivity more difficult.

D. Haemmerich, S. T. Staelin, J. Z. Tsai, "In vivo electrical conductivity of hepatic tumors," Physiological Measurement Vol. 24, pp. 251-260 (2003) discusses the use of conventional electrode methods to measure electrical conductivity of hepatic tumors to demonstrate that abnormal, or diseased, tissues exhibit different electrical properties than healthy tissues.

L. W. Hart, H. W. Ko, J. H. Meyer, D. P. Vasholz, and R. I. Joseph, "A noninvasive electromagnetic conductivity sensor for biomedical applications," IEEE Transactions on Biomedical Engineering, Vol. 35, No. 12, pp. 1011-1022 (1988) discusses the use of conductivity measurements to identify the presence of edema in brain tissues.

While various methods and apparatus for assessing health of human tissue using conductivity measurements have been developed, no design has emerged that generally encompasses all of the desired characteristics as hereafter presented in accordance with the subject technology.

SUMMARY

In one aspect of the present invention, a method of determining a vascular condition of an individual is disclosed. The method includes performing a first conductivity measurement of an extremity of the individual at a first elevation. The extremity of the individual may be an arm or may be a leg. After the first conductivity measurement is performed, the method includes elevating the extremity of the individual to a second elevation and performing a second conductivity measurement at the second elevation. For instance, the first elevation may be located substantially at or below the elevation of the heart of the individual and the second elevation may be located above the heart of the individual. The method further includes comparing the first conductivity measurement and the second conductivity measurement to determine a conductivity displacement $\Delta\sigma$ of the extremity responsive to the elevation change of the extremity. The conductivity displacement $\Delta\sigma$ may be used to determine a vascular condition of the individual.

In a variation of this particular aspect of the present invention, the conductivity displacement $\Delta\sigma$ may be used to determine whether a particular individual has peripheral artery disease. In other variations of this particular aspect of the present invention, conductivity displacement $\Delta\sigma$ may be used to monitor patient warming, to monitor circulatory shock, and/or to determine whether an individual has venous or arterial blockage.

In yet another variation of this particular aspect of the present invention, the method may further include performing a blood pressure measurement of the individual, such as, for example, a diastolic blood pressure measurement and/or a systolic blood pressure measurement. The blood pressure measurement may be used in conjunction with conductivity displacement $\Delta\sigma$ to determine a vascular condition of the individual.

In still another variation of this particular aspect of the present invention, the first and second conductivity measurements may be performed with a conductivity sensor comprising an induction coil. The induction coil may be configured to probe the specimen at a depth of up to about 15 mm below the skin of the individual. In particular aspects of the present invention, the induction coil comprises a first conductive element that spirals outward to an external perimeter and a second conductive element operably connected to the first conductive element. The second conductive element may spiral inward from the external perimeter staggered relative to the first conductive element. In other particular aspects of the present invention, the induction coil is part of a reactive circuit comprising a resistive element, a capacitive element, and the induction coil connected in parallel. The conductivity sensor may comprise a control circuit configured to drive the reactive circuit to resonance when the induction coil is measuring the conductivity of an extremity.

Another aspect of the present invention is directed to a method of assessing the health of a vascular system of an individual. The method includes performing a first conductivity measurement of an individual and then subjecting the vascular system of the individual to a stimulus. For example, in particular aspects of the present invention, the vascular system is subject to a stimulus by subjecting the individual to vigorous exercise. As used herein, the term "vigorous exercise" is intended to include exercise sufficient to cause the individual to expend energy greater than about 6 Metabolic Equivalent Tasks (METs). In variations of this particular aspect, the first conductivity measurement may be performed on an extremity at a first elevation and the second conductivity measurement may be performed on the extremity at a second elevation. The first elevation may be located substantially at or below the elevation of the heart of the individual and the second elevation may be located above the heart of the individual.

Another aspect of the present invention is directed to a method of assessing vascular health of an individual. The method includes maintaining the conductivity sensor adjacent to the individual and performing a series of conductivity measurements of the individual. The series of conductivity measurements include a plurality of conductivity measurements taken over a period of time. The method further includes using the series of conductivity measurements to determine the transient behavior of the conductivity of the individual over the period of time and using the transient behavior to assess the vascular health of the individual. As used herein, the term "transient behavior" of the conductivity of the individual refers to the behavior or variation in conductivity of the individual over a period of time.

In variations of this particular aspect of the present invention, the series of conductivity measurements is performed when the extremity is elevated above the heart of the individual. In particular aspects of the present invention, the plurality of conductivity measurements are performed at regular predetermined time intervals for the period of time.

Yet another aspect of the present invention is directed to a conductivity sensor for continuously monitoring the conductivity of an individual over a period of time. The conductivity sensor includes an induction coil for performing a conductivity measurement and a controller configured to direct the conductivity sensor to perform a series of conductivity measurements. The series of conductivity measurements include a plurality of conductivity measurements taken over a period of time. The conductivity sensor also includes a housing. The housing may be adapted to maintain the conductivity sensor adjacent to the individual while the series of conductivity measurements is being performed.

In variations of this particular aspect of the present invention, the conductivity sensor may include a database configured to store the series of conductivity measurements. In particular aspects, the conductivity sensor may include a communications device for communicating the series of conductivity measurements to a remote device. In still other particular aspects, the conductivity sensor may comprise an alert system for triggering an alert when a conductivity measurement of the plurality of conductivity measurements reaches a predetermined threshold.

In other variations of this particular aspect of the present invention, the housing of the conductivity sensor is adapted to be secured to the extremity of the individual. For example, the conductivity sensor may include a strap to secure the conductivity sensor to the extremity of the individual. In another particular aspect, the conductivity sensor may be secured to an individual by an adhesive material. In still other aspects, the conductivity sensor may be part of a medical sling used to support an extremity of an individual. In still other aspects, the conductivity sensor may be part of a garment or uniform worn by law enforcement or military personnel.

Still a further aspect of the present disclosure is directed to a platform unit for measuring the conductivity of an individual. The platform unit includes a base unit configured to support an individual standing on the platform unit and an induction coil for performing a conductivity measurement of a foot of the individual standing on the platform unit. The platform unit may include a visual display configured to display the conductivity measurement to the individual. In variations of this particular aspect, the platform unit may comprise a plurality of induction coils for performing a conductivity measurement of a foot of an individual standing on the platform unit.

These and other features, aspects and advantages of the present invention will become better understood with reference to the following description and appended claims. It is to be understood that different embodiments, as well as different presently preferred embodiments, of the present subject matter may include various combinations or configurations of presently disclosed features, steps, or elements, or their equivalents (including combinations of features, parts, or steps or configurations thereof not expressly shown in the figures or stated in the detailed description of such figures). Additional embodiments of the present subject matter, not necessarily expressed in the summarized section, may include and incorporate various combinations of aspects of features, components, or steps referenced in the summarized objects above, and/or other features, components, or steps as otherwise discussed in this application. Those of ordinary skill in the art will better appreciate the features and aspects of such embodiments, and others, upon review of the remainder of the specification.

BRIEF DESCRIPTION OF THE DRAWINGS

A full and enabling disclosure of the present invention, including the best mode thereof, directed to one of ordinary skill in the art, is set forth in the specification, which makes reference to the appended figures, in which:

FIG. 6b depicts a plan view of the exemplary conductivity sensor illustrated in FIG. 6a;

DETAILED DESCRIPTION

Figure 1:
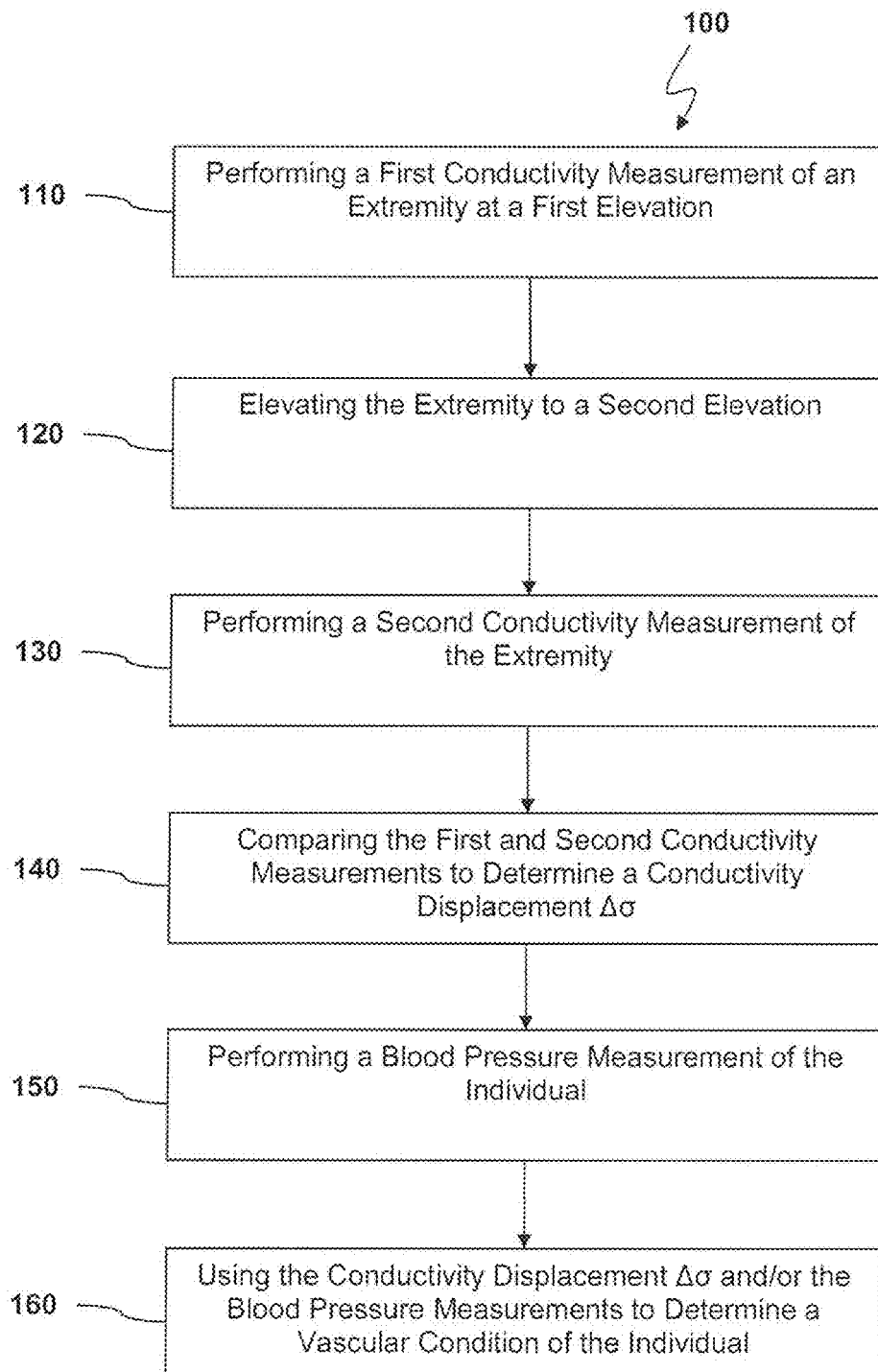
FIG. 1 depicts a flow diagram of the exemplary steps associated with an exemplary embodiment of the present invention.

In general, the present technology is directed to methods and apparatus for utilizing conductivity measurements to assess vascular health or to diagnose vascular conditions of an individual. For instance, certain embodiments of the present technology are directed to methods and apparatus that utilize conductivity measurements to diagnose peripheral artery disease, to monitor patient warming, to monitor circulatory shock, to monitor blood flow of an individual, to determine whether an individual has venous or arterial blockage, or to determine other vascular conditions or otherwise assess the vascular health of an individual.

Reference now will be made in detail to embodiments of the invention, one or more examples of which are illustrated in the drawings. Each example is provided by way of explanation of the invention, not limitation of the invention. In fact, it will be apparent to those skilled in the art that various modifications and variations can be made in the present invention without departing from the scope or spirit of the invention. For instance, features illustrated or described as part of one embodiment, can be used with another embodiment to yield a still further embodiment. Thus, it is intended that the present invention covers such modifications and variations as come within the scope of the appended claims and their equivalents.

The soft tissue directly beneath the skin consists primarily of a two-phase medium consisting of vascular tissue and interstitial fluids. The vascular tissue adjacent to the skin typically includes very small blood vessels such as, for example, capillaries, arterioles, and venules. This vascular tissue portion of human tissue is regarded as having a relatively low electrical conductivity. The low conductivity of the vascular tissue may be attributed to the insulating nature of capillary walls and the tendency for non-conductive blood cells to increase the path for charge carriers. Interstitial fluid conductivity, however, has been estimated to have a considerably higher conductivity than that of the capillaries. For instance, some studies have estimated the conductivity of interstitial fluids to be approximately 2.0 S/m.

Given that the ability of the capillary bed system to either contract or expand should depend on the stiffness of vessel walls and the contiguous tissues that surround the vessels, a technique for measuring tissue conductivity in response to changing vascular mechanical stresses should provide an effective approach for evaluation of vascular bed stiffness. Any stimulus, whether mechanical or physiological, that would cause the volume fraction of the vascular tissue to decrease would cause conductivity of the human tissue to increase. Similarly, any stimulus, whether mechanical or physiological, that would cause the volume fraction of the vascular tissue to increase would cause conductivity of the human tissue to decrease.

The effect of vascular tissue volume on human tissue conductivity can be explained with reference to Archie's law. Given that interstitial fluid has conductivity $\sigma_b$ and a volume fraction $\theta$, electrical conductivity of the soft tissue beneath the epidermis can be modeled by Archie's law as follows:

$$\sigma = a\sigma_b \left(\frac{\theta - \theta_c}{1 - \theta_c}\right)^2$$

where a, in most cases, is a dimensionless constant whose value depends on various factors.

Interstitial volume fraction must be above a critical value $\theta_c$ in order to have sufficient percolation for nonzero conductivity. Vascular volume fraction is equal to $1-\theta$. If interstitial volume fraction is well above critical volume fraction, electrical conductivity is expected to be quite sensitive to small changes in vascular tissue volume fraction.

There are natural situations that tend to cause blood vessels to either expand or contract. For example, capillaries in the extremities have a tendency to constrict when cooled, having the net effect of lowering the blood volume in the extremities. Thus, a measurement of conductivity in extremities that may have been chilled should contribute to an increase in conductivity due to a reduction in volume occupied by the capillary bed.

Another way to cause the vascular bed to constrict or expand is to change the elevation of the extremity relative to the heart. Elevation changes alter the nominal pressure of the fluid inside a blood vessel, easily causing pressure to change by 40 mm Hg, up or down. This is a significant fraction of normal blood pressure of about 120/80 mm Hg. In a healthy adult, elevation changes of the extremities should result in blood pressure swings that either increase or decrease vascular tissue volume, accompanied by the corresponding decrease or increase in conductivity, respectively.

The ability to sense changes in conductivity of human tissue due to volumetric changes of the vascular tissue volume will depend upon the inherent elasticity of the vascular system. Healthy adults experience blood volume changes in their extremities due to the ability of their blood vessels to expand and contract in response to stimuli, a feature needed in order to properly regulate blood pressure. If the vascular bed system is diseased, as it would be in the case of atherosclerosis, vessel walls become thickened and stiffened due to plaque deposits. The occurrence of atherosclerosis in the extremities is usually implicated with peripheral artery disease. Peripheral artery disease is a vascular condition that affects about one in three diabetics.

For those individuals suffering a significant loss in blood vessel elasticity, whether from peripheral artery disease or another condition, conductivity measurements of the extremities, performed while the extremity is alternately elevated above and below the heart, provide a measure of the severity of the condition. For instance, a healthy adult should expect electrical conductivity to increase in the forearm when elevated above the head, even after a short period of time. On the other hand, the individual afflicted with a vascular disease that stiffens the blood vessel system can expect much less, or perhaps no change in electrical conductivity in the extremities when they are elevated above the heart.

Another variable that tends to have an effect on the conductivity of an individual is the blood pressure of the individual. Individuals with higher blood pressure would tend to have a greater volume of blood flowing through the vascular bed system, even if subject to mechanical or physiological stresses that would tend to reduce blood volume in the extremities. Thus, blood pressure measurements used in conjunction with conductivity measurements in response to physiological and mechanical stimuli may provide an effective tool for analyzing vascular health.

The effect of elevation changes on human tissue conductivity measurements as well as the relationship between human tissue conductivity and various other variables, including both diastolic and systolic blood pressure, has been explored in detail and is discussed below with reference to Clinical Study #1 and Clinical Study #2.

Referring now to FIG. 1, the exemplary steps associated with a method 100 of determining a vascular condition of an individual will now be set forth. Step 110 of the method comprises performing a first conductivity measurement of an extremity of the individual at a first elevation. As used herein, the term extremity may refer to an individual's arm or leg. Reference to an "upper body extremity" refers to an arm of an individual while reference to a "lower body extremity" refers to a leg of an individual.

The conductivity measurement of step 110 may be performed using any device or apparatus configured to measure the conductivity of a specimen. For instance, the conductivity measurement may be performed with conventional electrodes or various induction coil devices. One such conductivity sensor that may be used in accordance with the present technology is disclosed in U.S. patent application Ser. No. 12/464,431, filed May 12, 2009, which is hereby incorporated by reference for all purposes.

As shown at step 120, after the first conductivity measurement has been performed, the method 100 comprises elevating the extremity of the individual to a second elevation. At step 130, the method 100 comprises performing a second conductivity measurement of the extremity at the second elevation. The second conductivity measurement may be performed after the extremity has been elevated at the second elevation for a period of time. For instance, the second conductivity measurement may be performed after the extremity has been elevated at the second elevation for a period of about 60 seconds, or about 45 seconds, or about 30 seconds, or about 120 seconds, or any other period of time. By elevating the extremity at the second elevation for a period of time prior to performing the second conductivity measurement, the vascular system of the individual has sufficient time to respond to stimulus provided by the elevation change of the extremity.

Similar to the first conductivity measurement, the second conductivity measurement may be performed using any device or apparatus configured to measure the conductivity of a specimen. Preferably the device or apparatus for performing the first conductivity measurement and the device or apparatus for performing the second conductivity measurement are the same to ensure accurate comparison of the first and second conductivity measurements.

The first and second elevations of the extremity may be any elevation attainable by the extremity so long as the first and second elevations differ to take advantage of a vascular bed volume change. In a particular embodiment, the first elevation is located substantially at the same or below the elevation of the heart of the individual and the second elevation is located above the heart of the individual. In this manner, the present technology may take advantage of the reduction in vascular bed volume caused by reduction in blood pressure of the elevated extremity.

In a particular embodiment, the first conductivity measurement may be performed while the individual's arm is extended or resting at a location substantially at the same or below the elevation of the heart of the individual while the second conductivity measurement is performed with the arm elevated above the head of the individual. In another exemplary embodiment, the first conductivity measurement may be performed on the individual's leg while the individual is lying down such that the individual's leg is located substantially at the same or below the elevation of the heart of the individual. The second conductivity measurement may be performed with the leg elevated upward so as to be located above the heart of the individual. For example, the second conductivity measurement may be performed when the leg of the individual is elevated in a medical sling.

At step 140, after performing the second conductivity measurement, the methodology of the present technology compares the first conductivity measurement and the second conductivity measurement to determine a conductivity displacement $\Delta\sigma$ of the extremity responsive to the elevation change of the extremity. The conductivity displacement $\Delta\sigma$ refers to the difference between the second conductivity measurement and the first conductivity measurement. As discussed in detail below, the conductivity displacement $\Delta\sigma$ may be used to diagnose a vascular condition of an individual.

For instance, in one embodiment, the conductivity displacement $\Delta\sigma$ may be used to monitor the progression of peripheral artery disease. As set forth in the discussion of Clinical Study #1 and Clinical Study #2 below, conductivity displacement $\Delta\sigma$ is proportional to vascular tissue flexibility. Conductivity displacement $\Delta\sigma$ should be greater for individuals with healthy vascular tissue that has not been stiffened by, for example, the onset of peripheral artery disease. Thus, because conductivity displacement $\Delta\sigma$ provides an indicator of vascular bed flexibility, analysis of conductivity displacement $\Delta\sigma$ according to the present technology provides a useful tool for monitoring the progression of peripheral artery disease in an individual. Other applications of the present method may be for monitoring patient cooling, monitoring progression of circulatory shock, to monitor blood flow or blood volume of an individual, and/or to determine whether an individual has arterial or venous blockage of the vascular system.

In a variation of this embodiment, the method 100 may further comprise taking blood pressure measurements of the individual, as illustrated at step 150. The blood pressure measurements may include both systolic and diastolic blood pressure measurements performed by conventional methods known in the art. The method 100 may use the blood pressure measurements in conjunction with conductivity displacement $\Delta\sigma$ to assess a vascular condition of the individual, as shown at step 160. For example, as set forth in detail in the discussion of Clinical Study #1 and Clinical Study #2, those with lower diastolic blood pressure should exhibit a more notable conductivity displacement $\Delta\sigma$ in response to elevation of an extremity, while those with high systolic blood pressure should exhibit little or no conductivity displacement $\Delta\sigma$.

As another example, conductivity displacement $\Delta\sigma$ may also be used in conjunction with blood pressure measurement to determine whether an individual has venous or arterial blockage. For example, as discussed in Clinical Study #2 below, any individual displaying high blood pressure and displaying a significant conductivity displacement $\Delta\sigma$ is suspect for some measure of arterial blockage.

Figure 2:
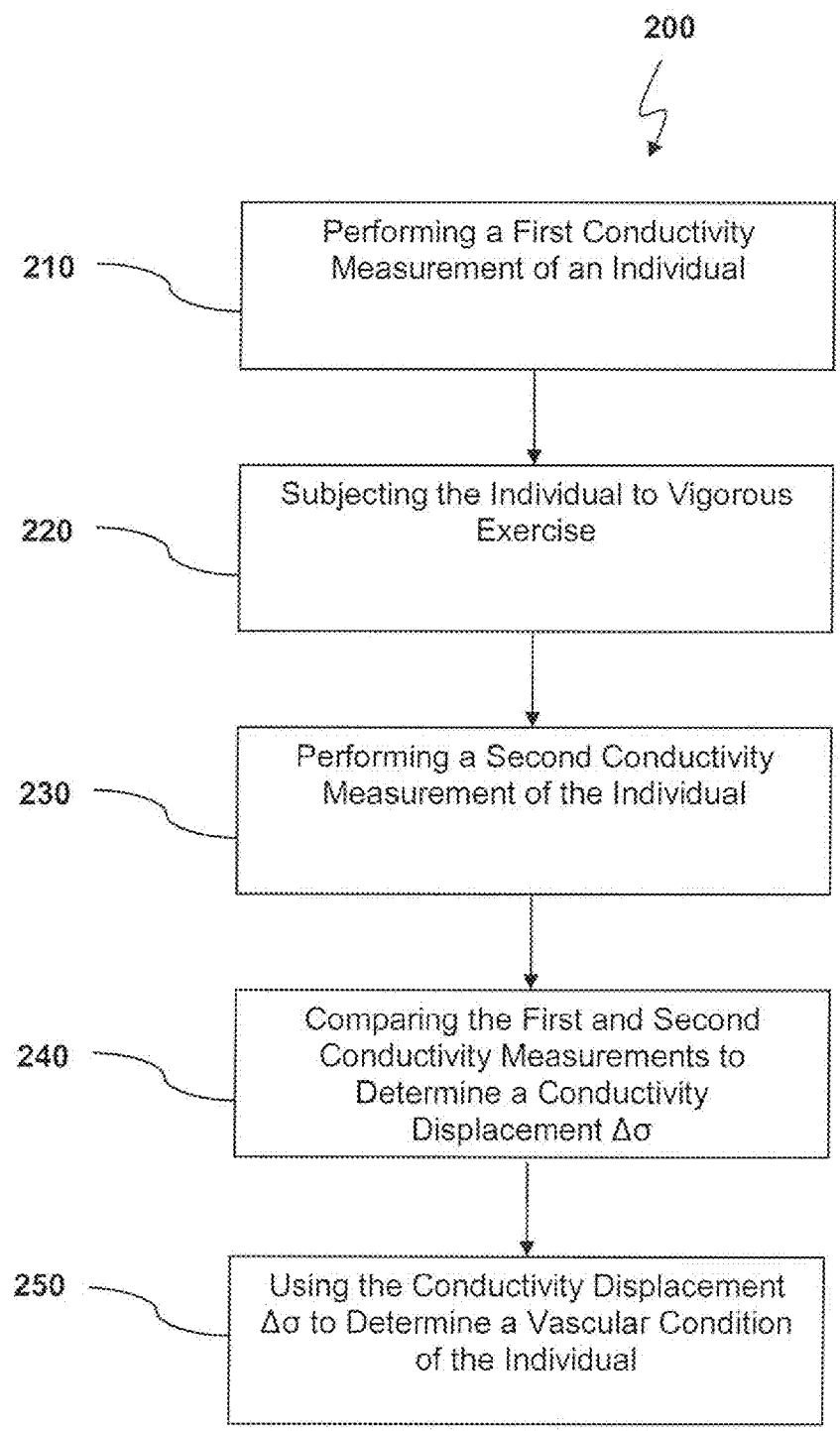
FIG. 2 depicts a flow diagram of the exemplary steps associated with another exemplary embodiment of the present invention

With reference now to FIG. 2, another exemplary embodiment of the present invention will now be set forth. As shown at step 210, the method 200 includes the step of performing a first conductivity measurement of an individual The conductivity measurement of step 210 may be performed using any device or apparatus configured to measure the conductivity of a specimen.

After the conductivity measurement is performed, the method 200 includes subjecting the vascular system of the individual to a stimulus. The stimulus may be any physiological stimulus or a mechanical stimulus that causes a change in the vascular blood flow through the vascular system of the individual. For example, in one embodiment, the stimulus may be elevating an extremity of the individual to an elevation above the heart of the individual.

In a particular embodiment, the step of subjecting the vascular system of the individual to a stimulus is performed by subjecting the individual to vigorous exercise (step 220 of FIG. 2). As used herein, the term "vigorous exercise" is defined to include exercise sufficient to cause the individual to expend energy greater than about 6 Metabolic Equivalent Tasks (METs). The individual may be subjected to vigorous exercise, for example, by requiring the individual to perform aerobic exercise(s) such as running, jogging, walking, cross-training, cross-country skiing, rowing, or any other activity which increases the heart rate of the individual. In particular embodiments, the vigorous exercise may be performed on a variety of equipment, including, for example, treadmills, elliptical machines, rowing machines, stationary bikes, stair climbers, nautilus equipment, or any other equipment.

After the vascular system of the individual has been subjected to a stimulus, such as by subjecting the individual to vigorous exercise, the method 200 includes the step 230 of performing a second conductivity measurement of the individual. Similar to the first conductivity measurement, the second conductivity measurement may be performed using any device or apparatus configured to measure the conductivity of a specimen. Preferably the device or apparatus for performing the first conductivity measurement and the device or apparatus for performing the second conductivity measurement are the same to ensure accurate comparison of the first and second conductivity measurements.

At step 240, after performing the second conductivity measurement, the method 200 compares the first conductivity measurement and the second conductivity measurement to determine a conductivity displacement $\Delta\sigma$ of the individual responsive to the stimulus. The conductivity displacement $\Delta\sigma$ refers to the difference between the second conductivity measurement and the first conductivity measurement. At step 250, the conductivity displacement $\Delta\sigma$ is used in accordance with the teachings herein to assess the health of the vascular system of the individual.

In many cases, it may be desirable to continuously monitor the conductivity of human tissue over a period of time to determine the transient behavior of the conductivity of the extremity. The transient behavior of the conductivity may be particularly useful in determining whether a patient or other individual is warming properly, is going into circulatory shock, or whether blood is flowing properly to the extremities of the individual. For instance, if the conductivity of a person suddenly increases to a particular level, this indicates that the vascular bed volume in the extremity has undergone a sudden decrease, indicating that the individual may be entering into circulatory shock.

Figure 3:
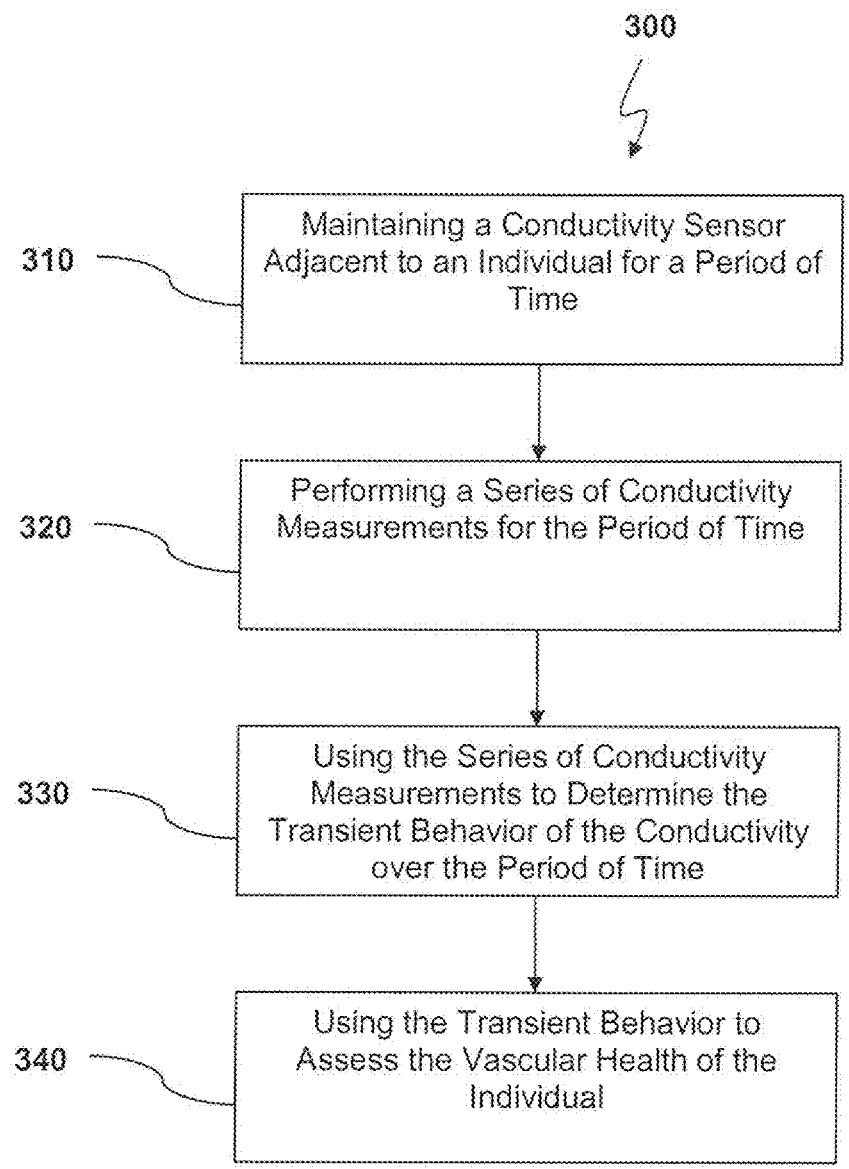
FIG. 3 depicts a flow diagram of the exemplary steps associated with yet another exemplary embodiment of the present invention.

To address these concerns, an alternate embodiment of the present invention is directed to a method of assessing vascular health. With reference now to FIG. 3, the exemplary steps associated with this exemplary methodology 300 of the present invention will now be set forth. At step 310, the method comprises maintaining a conductivity sensor adjacent to an individual for a period of time. Similar to the methodology 100 set forth in FIG. 1 and discussed above, the conductivity sensor for this exemplary embodiment may be any device or apparatus for measuring the conductivity of the extremity.

At step 320, while the conductivity sensor is maintained adjacent to the individual, a series of conductivity measurements are performed on the extremity. The series of conductivity measurements comprise a plurality of conductivity measurements taken over the period of time. The plurality of conductivity measurements may be taken at regular intervals according to programmed instructions, or may be taken at irregular intervals. The series of conductivity measurements may be performed on an extremity located at any elevation. In a particular embodiment, the series of conductivity measurements are performed on an extremity that is elevated above the heart of the individual when the vascular tissue volume of the extremity is particularly sensitive to mechanical or physiological stresses.

At step 330, the methodology 300 according to this exemplary embodiment uses the series of conductivity measurements to determine the transient behavior of the conductivity over a period of time. The transient behavior of the conductivity may be used at step 340 to monitor or assess the vascular health of the individual.

For example, in one embodiment, the transient behavior may be used to monitor patient warming. When body temperature has dropped to dangerously low levels, blood circulation into the extremities is reduced. As the patient warms, the blood volume will return to the extremities, resulting in a decrease in the conductivity of the extremity. Analysis of the transient behavior of the conductivity of an extremity may thus be useful to determine the effectiveness of patient warming.

In another embodiment, the transient behavior may be used to monitor the onset of circulatory shock in an individual. Circulatory shock is a condition where insufficient blood flow reaches the body tissues. During the onset of circulatory shock, conductivity measurements of body tissue would be expected to increase as less blood is flowing to the tissue. Thus, analysis of the transient behavior of the conductivity of an extremity may be useful to monitor the onset of circulatory shock.

Another application of the present technology would be in combat scenarios, law enforcement scenarios, or other scenarios where individuals may be placed in danger of harm resulting in the loss of blood. The individual may be required to wear a conductivity sensor as part of his or her uniform that monitors the conductivity of the individual. If the conductivity reaches a certain threshold, the conductivity sensor may send an alert to medical personnel warning that a person may be about to enter into circulatory shock.

Other applications of the present technology may include probing for intubation sites, probing for surgical site infection, monitoring circulation during medical procedures or recovery or a variety of other applications.

Conductivity measurements according to the methodology of the present technology may be performed with any apparatus or device for measuring conductivity. A block diagram of an exemplary conductivity sensor 400 is provided in FIG. 4. As illustrated, exemplary conductivity sensor 400 includes an induction coil 410 that may or may not be part of a reactive circuit 420, a control circuit 440 with controller 430, a database system 450, a communications device 460, and an alert system 470.

The induction coil 410 may be configured to perform a conductivity measurement by generating an electric field that generates eddy currents in a conductive specimen. The sensor 400 may be configured to measure conductivity of the specimen using techniques described in detail in U.S. patent application Ser. No. 12/464,431, filed May 12, 2009, which is incorporated herein by reference for all purposes.

In particular embodiments, the conductivity sensor may perform conductivity measurements with a conductivity sensor having an induction coil that probes the human tissue specimen at depths such as to avoid interferences from bone and internal organs. For instance, the induction coil may be configured to probe the extremity up to about 15 mm below the skin of the individual.

Figure 5A:
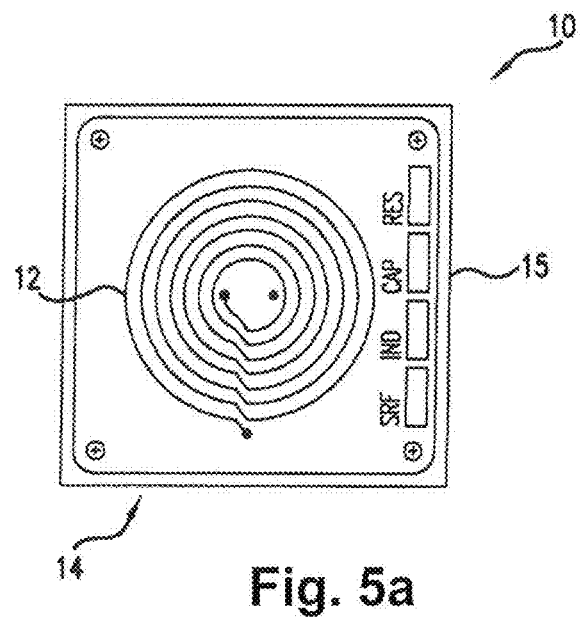
FIG. 5a depicts a plan view of an exemplary induction coil in accordance with an exemplary embodiment of the present invention.

Such an exemplary induction coil is illustrated in FIG. 5*a*. The induction coil 10 includes a conductive element 12 disposed on a circuit board 15. Circuit board 15 may be a printed circuit board or any other board that is adapted or configured to mechanically support the conductive element 12. The circuit board 15 supports conductive element 12 on opposing first and second sides of the circuit board 15. First side 14 of circuit board 15 is illustrated in FIG. 5*a*.

Figure 5B:
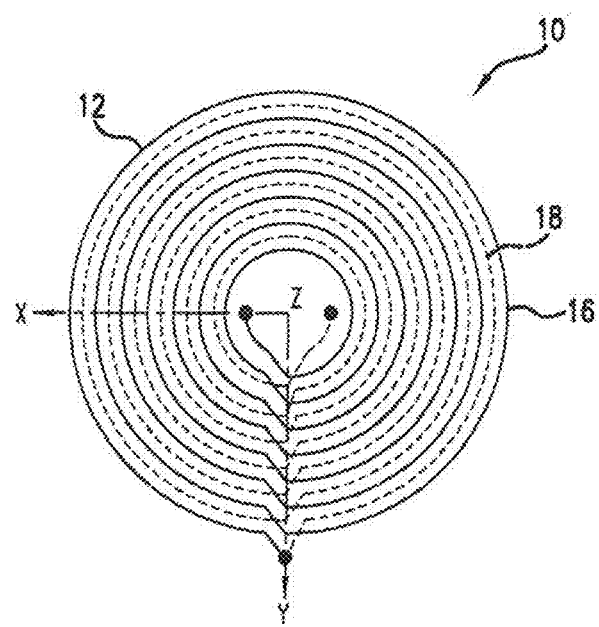
FIG. 5b depicts a plan view of the exemplary induction coil shown in FIG. 5a showing the second conductive element spiraling inward staggered relative to the first conductive element.

As shown in FIG. 5*b*, conductive element 12 includes a first conductive element 16 spiraling outward on the first side 14 of the circuit board 15 and a second conductive element 18 spiraling inward on the second side of the circuit board 15. The second conductive element 18 spirals inward staggered relative to the first conductive element 16. In the embodiment shown in FIG. 5*b*, the first conductive element 16 spirals outward to an external diameter, passes to the other side of the circuit board 15, and then spirals inward as the second conductive element 18. The second conductive element 18 is staggered relative to the first conductive element 16.

The probing depth of the induction sensor may be varied by altering the dimensions of the induction coil or by adjusting the resonant frequency of the induction coil reactive circuit. For instance, the external diameter of the induction coil 10 may be in the range of about 5 mm to 120 mm, such as about 10 mm to 80 mm, such as about 30 mm to 40 mm, such as about 35 mm, or about 38 mm, or any other diameter or range of diameters therebetween. The inductance of the induction coil may be in the range of about 3 to 4 microH, such as about 3.2 to 3.6 microH, such as about 3.4 microH, 3.5 microH, or any other inductance or range of inductance therebetween. The inter-winding capacitance of the induction coil may be about 10 pF. The self-resonance point of the induction coil would be approximately 27 MHz. In this particular embodiment, if additional parallel capacitance is added to adjust the resonant frequency to about 15 MHz, the electric field generated by the induction coil should penetrate to no more than a depth of approximately 15 mm, avoiding interferences from bone and internal organs.

Figure 4:
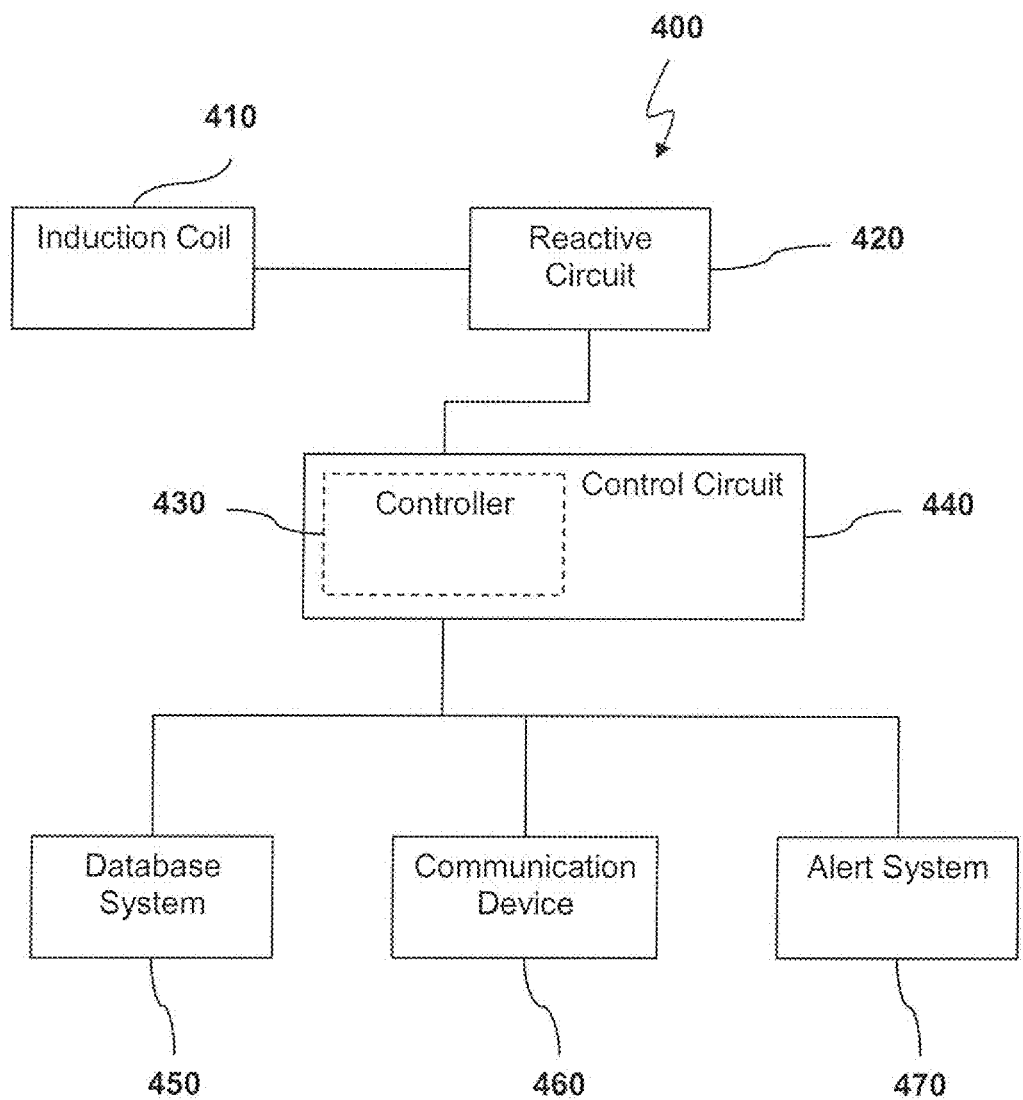
FIG. 4 provides a block diagram of an exemplary conductivity sensor according to an exemplary embodiment of the present invention.

Referring still to FIG. 4, induction coil 410 may be a part of or coupled with reactive circuit 420. In a particular embodiment, the reactive circuit 420 may include a resistive element, a capacitive element, and the induction coil connected in parallel. The conductivity sensor may have a control circuit 440 adapted to drive the reactive circuit 320 to resonance when the induction coil 410 is maintained adjacent to the individual. Such an exemplary induction coil conductivity sensor is described in detail in U.S. patent application Ser. No. 12/464,431, filed May 12, 2009, which is incorporated herein by reference for all purposes.

The control circuit 440 and the controller 430 form the central processing and control circuitry of exemplary conductivity sensor 400. The control circuit 440 may include various devices for maintaining the reactive circuit at resonance when the induction coil is placed adjacent to the specimen. The controller 430 is the main processing unit of the conductivity sensor 400. The controller 430 may be configured to direct the conductivity sensor to perform a plurality of conductivity measurements at predetermined regular or irregular intervals over a period of time. In this manner, the conductivity sensor 400 may be used to perform a series of conductivity measurements of a specimen over a period of time to determine transient effects of the conductivity of the specimen. This type of conductivity sensor is particularly useful for monitoring vascular health of an individual.

Referring still to FIG. 4, conductivity sensor 400 may include a database system 450 operably connected to controller 430. The database system 450 may be configured to store conductivity measurements made by the conductivity sensor for future use and analysis. For example, the conductivity sensor 400 may be directed by controller 430 to perform a series of conductivity measurements over a time period of three hours at a rate of one conductivity measurement per second. As another example, the conductivity sensor 400 may be directed by controller 430 to perform a series of conductivity measurements over a period of 60 seconds at a rate of 1 conductivity measurement every 10 ms. Those of ordinary skill in the art, using the teachings disclosed herein, will understand that the present invention is not limited to any particular time period or time intervals between conductivity measurements. The database system 450 will store each of the conductivity measurements performed during the time period so that the conductivity measurements can be later analyzed to determine transient effects.

Referring still to FIG. 4, conductivity sensor 400 may include a communications device 460 operably connected to the controller 430. The controller 430 may interact with communications device 460 to interface with various remote devices, such as remote laptop computers. For example, the controller may interact via a Bluetooth® wireless communication module to interface data collection and control application with a remote computer. The Bluetooth® wireless communication interface may be a Bluegiga WT12 Bluetooth® module that allows full duplex serial communications between the remote device and the controller 430. The controller 430 may also communicate via one or more communications networks. It should be appreciated that the communications device or medium can include one or more networks of various forms. For example, a network can include a dial-in network, a local area network (LAN), wide area network (WAN), public switched telephone network (PSTN), the Internet, intranet or other type(s) of networks. A network may include any number and/or combination of hard-wired, wireless, or other communication links.

Still referring to FIG. 4, the controller 430 may be operably connected to alert system 470. Alert system 470 may be configured to provide a visual or audible alarm when the conductivity of a specimen reaches a certain threshold. For example, in a particular embodiment, the alert system 470 could be configured to light up an LED device when the conductivity of the specimen reaches a certain threshold. In another embodiment, the alert system 470 could be configured to sound an audible alarm when the conductivity of the specimen reaches a certain threshold. In still another embodiment, the alert system 470 could provide notification to remote personnel through communications device 460 when the conductivity of the individual reaches a certain threshold.

Figure 6A:
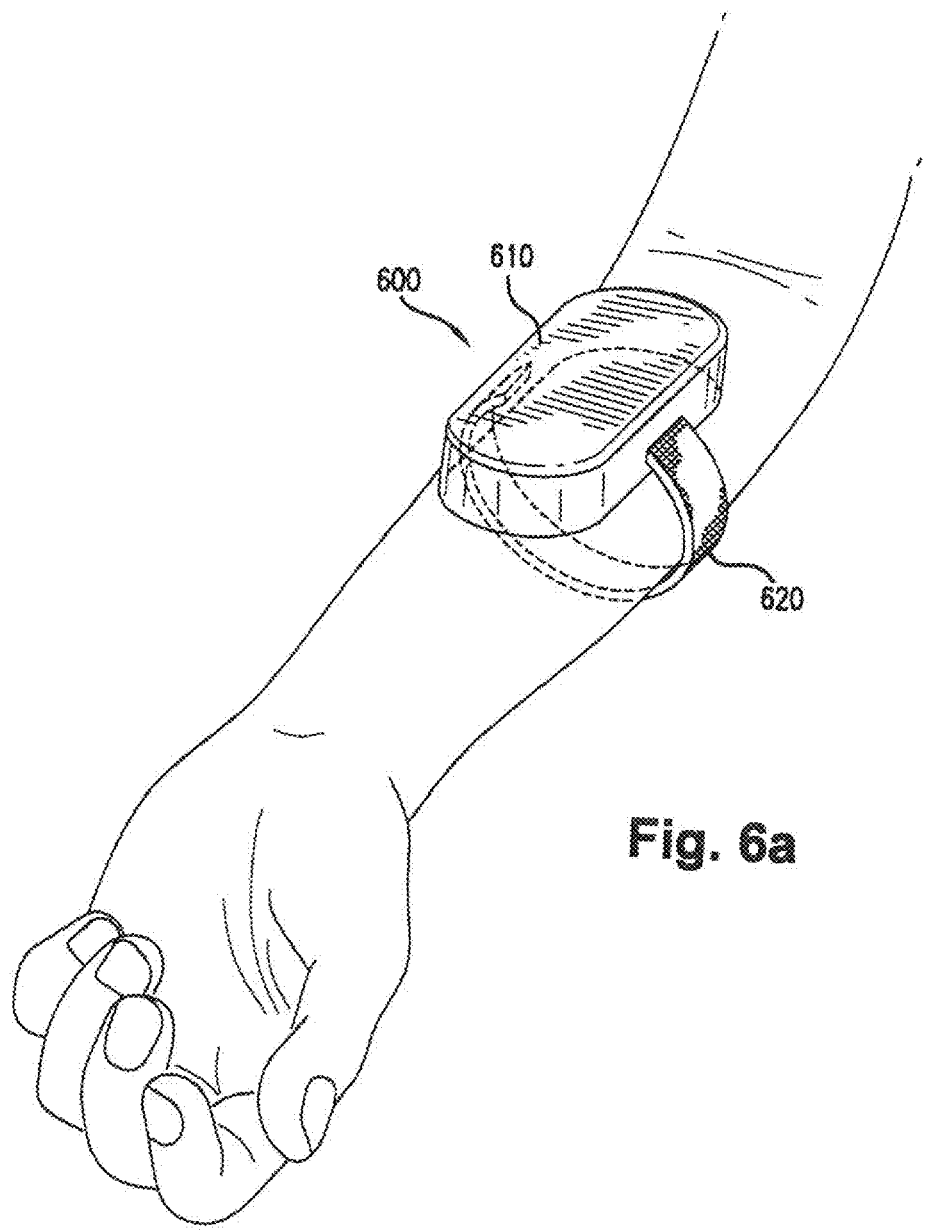
FIG. 6a depicts an exemplary conductivity sensor adapted to be maintained adjacent to an extremity of an individual according to one embodiment of the present invention.
Figure 6B:
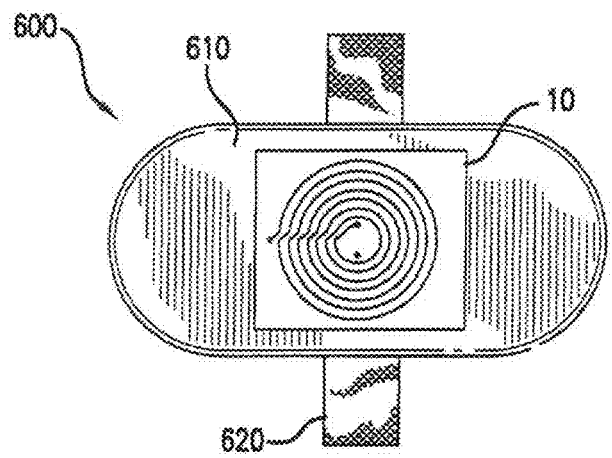

Conductivity sensors according to the present technology may be packaged in a variety of forms, depending on the intended application of the conductivity sensor. For instance, as illustrated in FIGS. 6a and 6b, conductivity sensor 600 may be packaged into a compact housing 610. As used herein, the term "compact housing" refers to any housing that has a length of less than about 25 cm, such as less than about 15 cm, such as less than about 10 cm. Compact housing 610 stores all necessary electronics and circuitry for operation of the conductivity sensor 600, including any database for storage of conductivity measurement data, communications device for interfacing with remote devices, and alert systems for providing an alert if the conductivity measurement reaches a certain threshold.

The compact conductivity sensor 600 illustrated in FIG. 6a may be maintained adjacent to an individual using any structure or materials for affixing or securing the conductivity sensor 600 to the individual. For example, as illustrated in FIG. 6a, conductivity sensor 600 may include a strap 620 that is used to secure the conductivity sensor to the arm of the individual. In another embodiment, the conductivity sensor 600 may be maintained adjacent to the individual by use of an adhesive material. Such adhesive material may include medical grade skin adhesives such as 3M Double Coated Spunlace Nonwoven Tape 9917 manufactured by the 3M Company and/or 3M Transfer Adhesive 1524 manufactured by the 3M Company. By maintaining the conductivity sensor 600 adjacent to the individual, the conductivity sensor may perform a series of conductivity measurements on the specimen for a period of time. The conductivity sensor 600 may be particularly useful for continuously monitoring the conductivity of the extremity of an individual to determine transient effects of the conductivity of the individual.

FIG. 6b depicts a plan view of the conductivity sensor 600 illustrated in FIG. 6a. As shown, conductivity sensor 600 includes an induction coil 10 similar to induction coil 10 illustrated in FIG. 5a and FIG. 5b. The housing 610 and strap 620 are used to continuously maintain the induction coil 10 adjacent to the specimen to continuously monitor the conductivity of the specimen.

In another exemplary embodiment of the present invention, the conductivity sensor is used as part of a medical sling for elevating an extremity of the individual. The sling may comprise a conductivity sensor 400 similar to that shown in FIG. 4 for continuously monitoring the conductivity of the extremity. If the conductivity of the extremity reaches a certain threshold caused for example by a drop in blood circulation in the extremity, the conductivity sensor may be adapted to provide an indication or alert indicating that the conductivity of the extremity has reached a certain threshold.

In another exemplary embodiment of the present invention, the conductivity sensor may be incorporated into a garment or uniform. Such a conductivity sensor would be particularly useful in combat scenarios, law enforcement scenarios, or other scenarios where individuals may be placed in danger of harm resulting in the loss of blood. The uniform or garment may comprise a conductivity sensor 400 similar to that shown in FIG. 4 for continuously monitoring the conductivity of the extremity. If the conductivity of the individual wearing the garment or uniform reaches a certain threshold, the conductivity sensor may send an alert to medical personnel warning that a person may be about to enter into circulatory shock.

Figure 7:
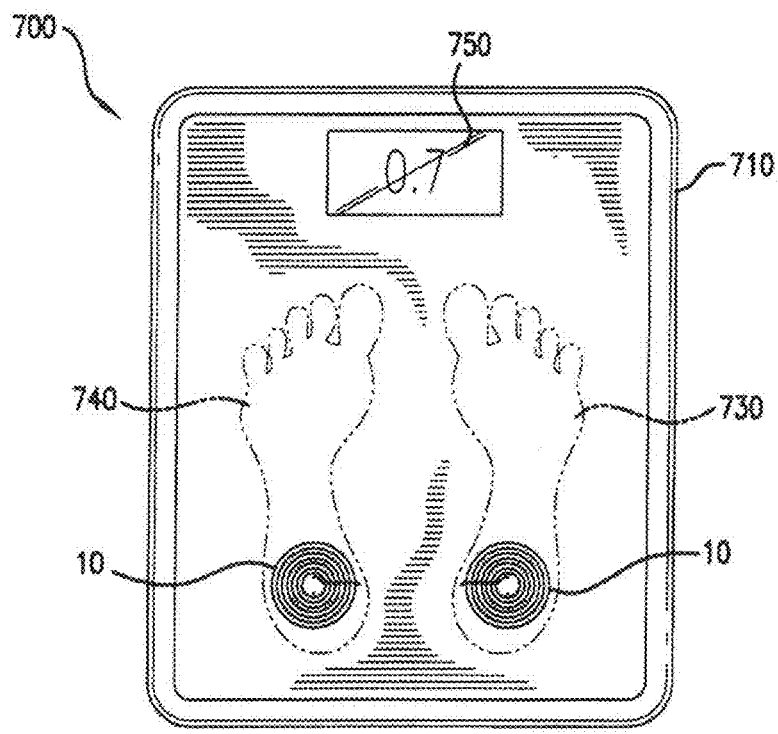
FIG. 7 depicts an exemplary platform unit according to one exemplary embodiment of the present invention.

Referring now to FIG. 7, a platform unit 700 for measuring the conductivity of an individual is disclosed. The platform unit includes a base 710 configured to support an individual standing on the platform unit 700. The base unit 710 may enclose all of the necessary electronics and circuitry for operation of the platform unit 700, including any database for storage of conductivity measurement data, communications device for interfacing with remote devices, and alert systems for providing an alert if the conductivity measurement reaches a certain threshold.

As illustrated, the platform unit 700 includes two areas 730 and 740 for receiving a person's feet standing on the platform unit 700. Located within the areas 730 and 740 are induction coils 10. Induction coils 10 may be similar to induction coil 10 illustrated in FIG. 5a and FIG. 5b. When a person stands on the platform unit 700, induction coils 10 perform a conductivity measurement of the person's feet. The conductivity measurement is displayed to the individual through visual display 750. In particular embodiments, the conductivity measurements may be stored in a database, communicated to a remote device, or used to trigger an alarm if the conductivity measurement is at or beyond a certain threshold.

The platform unit 700 allows an individual to periodically perform conductivity measurements using a simple device that is similar to a typical scale found in a person's home. An individual with vascular health issues could use platform unit 700 to periodically monitor the individual's vascular health from the convenience of the individual's home.

Clinical Study #1

A first clinical study was conducted to measure electrical conductivity of human tissue at a variety of sites on the human body in regions extending below the skin surface to a depth of about 15 mm to ultimately determine normal conductivity levels for healthy adults. In this study, 40 healthy adults having ages ranging from 25 to 45 were selected. This group of adults included 16 adult men and 24 adult women. Conductivity measurements were made in triplicate on seven locations on each side of the body, including: (1) mid-volar forearm (M); (2) proximal volar forearm (P); (3) inside upper arm (U); (4) lumbrosacral (lower back) (S); (5) inside mid-thigh (T); (6) back of calf (C); and (7) bottom of foot (ball) (F). A final measurement, one replicate only, was taken at the mid-volar forearm of the right arm after it was kept elevated above the head for 60 seconds.

Conductivity measurements were performed using a conductivity sensor of the type described in detail in U.S. Application Ser. No. 12/464,431, filed May 12, 2009 which is incorporated herein by reference for all purposes.

Each subject was asked to visit the clinic a total of four times for a complete set of measurements. At the first visit to the clinic, marks were made with a surgical pen to facilitate return to the same location at later visits, as well as from one replicate to the next. The first two sets of measurements, taken four hours apart, preceded by two weeks the third and fourth sets, also spaced four hours apart. During measurement, subjects were able to sit comfortably on an examination table, with torso upright and legs extended at the same elevation as the hips. Prior to collecting a set of measurements, subjects were given 15 minutes to relax and acclimate to surroundings. Temperature in the exam room was held at about 72° F. while humidity was kept at about 40%.

Subjects were judged healthy provided that they were non-smokers, not too overweight (Body Mass Index less than 27) and not routinely under medication for the treatment of cardiovascular issues. In addition to conductivity measurements, the following were also measured: weight, height, blood pressure (both arms), urine specific gravity, pulse, BMI, percent body water, percent body fat, and bone mass. Blood pressures in both arms were measured because of known discrepancies between right and left due to vascular disease. In addition, age, and for women, dates of last menstruation were recorded. Table 1, provided below, provides a summary of data obtained during the study.

TABLE 1

| Location | Women Avg. Conductivities (S/m) | | | | Men Avg. Conductivities (S/m) | | | |
| --- | --- | --- | --- | --- | --- | --- | --- | --- |
| | L | L-std | R | R-std | L | L-std. | R | R-std. |
| M | 3.82 | 0.36 | 3.74 | 0.39 | 3.4 | .24 | 3.3 | 0.26 |
| P | 3.94 | 0.32 | 3.9 | 0.39 | 3.56 | .26 | 3.53 | 0.23 |
| U | 4.04 | 0.46 | 3.84 | 0.4 | 3.7 | .35 | 3.46 | 0.3 |
| S | 2.97 | 0.28 | 3.2 | 0.32 | 2.83 | .17 | 3.01 | 0.31 |
| T | 3.99 | 0.36 | 3.66 | 0.29 | 3.43 | .36 | 3.13 | 0.31 |
| C | 3.69 | 0.27 | 3.65 | 0.25 | 3.21 | .27 | 3.17 | 0.24 |
| F | 3.55 | 0.41 | 3.75 | 0.5 | 3.49 | .35 | 3.59 | 0.34 |
| Overall: | 3.71 | 0.35 | 3.68 | 0.36 | 3.37 | .29 | 3.31 | 0.28 |

Table 1 summarizes the various averages obtained by gender and location. As the data indicate, the difference between the left and the right sites is small, except for the inner thigh, where it is nearly 10% higher for both male and female subjects on the left thigh site.

Figure 8:
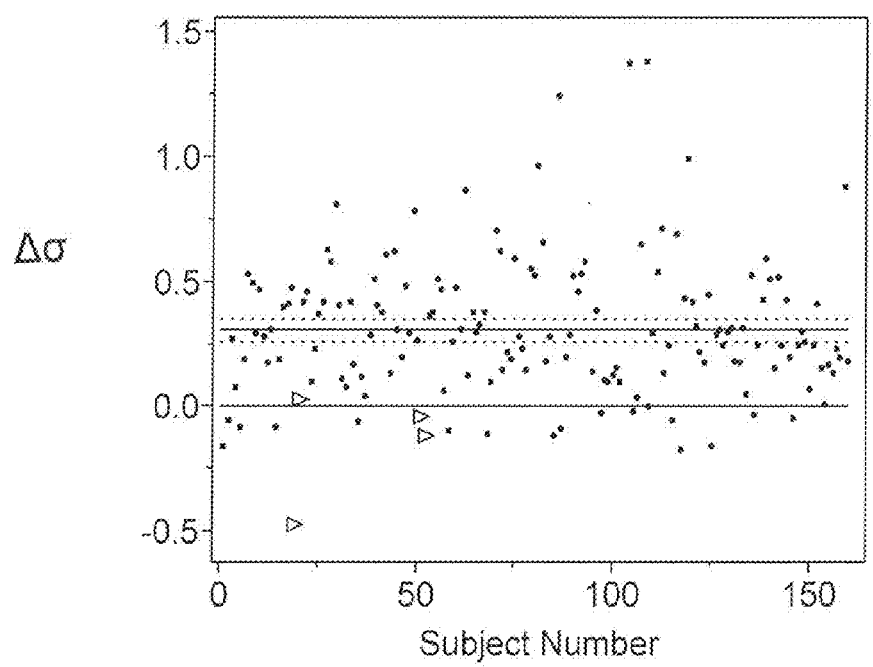
FIGS. 8-11 depict data obtained during Clinical Study #1 and Clinical Study #2 discussed below.

A primary hypothesis of the study was that electrical conductivity ought to increase as the vascular bed volume decreases. In FIG. 8, the results of a matched pair test comparing right arm elevated above the heart to not elevated are illustrated. As shown, increased conductivity is generally observed while elevating the right arm, in the amount of 0.33 S/m averaged over all subjects. The two highest data points in the figure were discarded from the analysis as they were obtained from incorrect technique. As the analysis shows, there is a 95% chance that conductivity displacement Δσ data fall within the range of 0.276 S/m to 0.384 S/m.

The remainder of Clinical Study #1 was directed to determining whether there was a relationship between conductivity and conductivity displacement Δσ and weight, height, blood pressure (both arms), urine specific gravity, pulse, BMI, percent body water, percent body fat, and bone mass. The results of Clinical Study #1 include: (1) conductivity is nominally about 0.36 S/m higher for women than men; (2) conductivity decreases with age at all body locations when all other subject variables are held fixed; (3) conductivity decreases with increased systolic blood pressure at all body sites, all other variables fixed; (4) for most locations, conductivity steeply decreases with increased percent body water.

Clinical Study #2

A second study was conducted to incorporate a more extensive examination of the role of extremity elevation on conductivity. The second clinical study allowed for a broad array of subjects that includes smokers and spans a wide range of ages and BMI (Body Mass Index). Selection of the subjects was based upon a desire to increase the likelihood of encountering individuals exhibiting compromised vascular health and to reveal different patterns of conductivity displacement for healthy and health impaired individuals. Only male subjects were included because men are more likely to exhibit symptoms of peripheral artery disease.

The study included 39 subjects which were divided into six groups, with Group 1 judged to be the most healthy and Group 6 judged to be the least healthy. Ranking was based upon three factors: age, BMI, and smoking. Smoking was quantified according to whether a subject smoked more than two cigarettes per day, or had not been smoking at all for at least 10 years. Table 2 below shows the distribution of groups and how they were ranked according to risk.

TABLE 2

| DOE Grid | Non Smoker | Smoker |
| --- | --- | --- |
| Age Range: | 25-35 | 36-70 | 40-70 |
| BMI < 28 | 7 (1) | 5 (2) | 7 (5) |
| BMI >= 28 | 5 (3) | 7 (4) | 8 (6) |

Total of 39 Male Subjects; Six Categories

Numbers provided in the parentheses designate both the Group Number and the risk level assigned to that group, with one the lowest and six the highest.

Through further evaluation of individuals, additional risk factors were identified. These included: high blood pressure (HBP); asymmetric blood pressure (ABP); and diabetes. Generally, a subject was viewed as having high blood pressure if systolic blood pressure in both arms and during both visits exceeded 120 mm Hg. A subject was considered to have an asymmetry in blood pressure if the difference in average systolic blood pressure between left and right arms exceeded 5 mm Hg. Studies have shown peripheral artery disease to be significantly more prevalent in those with asymmetric blood pressure. A subject was considered to have diabetes if that information was volunteered—no effort was made to verify a diabetic condition. Four subjects claimed to have diabetes. Subject distribution across the six risk groups is shown below in Table 3.

TABLE 3

| Group | Number of Subjects | Subjects with High BP | Subjects with ABP | Subjects with High BP/ABP |
| --- | --- | --- | --- | --- |
| Group 1 | 7 | 1 | 4 | 0 |
| Group 2 | 5 | 1 | 1 | 1 |
| Group 3 | 5 | 1 | 5 | 1 |
| Group 4 | 7 | 5 | 2 | 2 |
| Group 5 | 7 | 4 | 1 | 0 |
| Group 6 | 8 | 6 | 2 | 1 |

Though an effort was made to have equal numbers of subjects in each group, this became impractical due to no-shows and last minute efforts to fill in vacated spots. Furthermore, it may well be argued that BMI less than 28 is not sufficiently restrictive to populate group one—the most "healthy group". Given the high incidence of an overweight condition in the local community, finding subjects with BMI less than or equal to 25 proved difficult. BMI breakdown for group one was: 21.5, 21.6, 25.1, 25.5, 26.1, 27.1 and 27.4.

In addition to electrical conductivity measurements, additional data recorded for each subject included: age, height, weight, left and right arm blood pressures, pulse, urine specific gravity, BMI, bone mass, percent body water, percent body fat, smoking, time of conductivity measurement. As may be expected, these 15 "subject variables" were not completely independent of each other. Principal component analysis (PCA) revealed that only about six of these are needed to capture subject variability contained in the set.

Electrical conductivity measurements were taken at seven sites, on each side of the body, for a total of 14 first elevation measurements: 1) mid volar forearm; 2) proximal volar forearm; 3) inside upper arm; 4) lumbosacral; 5) inside thigh; 6) back of calf; 7) ball of foot. Each of these sites was measured in triplicate—all 14 sites were visited in turn prior to returning to the same site for replication. Forearm measurements were obtained with the forearm in a hanging position. The subject sat on an examination table, with back unsupported and legs extended at about the elevation of the hips.

Conductivity measurements were performed using a conductivity sensor of the type described in detail in U.S. application Ser. No. 12/464,431, filed May 12, 2009 which is incorporated herein by reference for all purposes.

Once all regular replicates were obtained, measurements on elevated extremities at a second elevation were made in triplicate, with all replicates obtained at the same time. These included: a) raised proximal volar forearms, both left and right while in the sitting position; b) raised calves, both left and right with the subject lying flat on his back; c) calves while in the standing position. For each of the elevated positions, or for the standing position, the subject remained in that position for 30 seconds prior to electrical conductivity measurement. While in the standing position, subjects were asked to distribute their weight equally on both feet. When measurement was made on one leg, the subject was asked to put their weight entirely on the other leg to relax the calf muscle being measured. Throughout the two weeks of the clinical, room temperature was maintained about 68° F. Prior to any conductivity measurements, subjects were detained in the testing room for about 15 minutes to promote acclamation.

Figure 9:
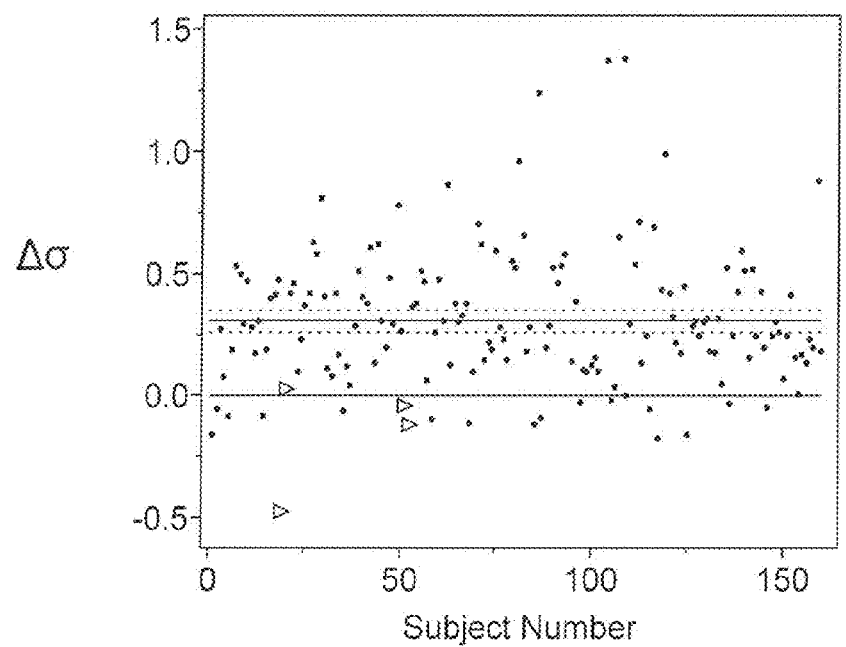

Before considering elevation effects in data obtained in Clinical Study #2, the results of Clinical Study #1 are first considered. In Clinical Study #1, discussed above, it was observed that electrical conductivity at the right mid volar forearm rose by a significant amount after 60 seconds of elevation in nearly all subjects, whether male or female. FIG. 9 illustrates the effect for both genders, where change in conductivity is plotted against subject number (each subject was measured at four different times). Given that the standard deviation associated with conductivity measurement at the mid volar forearm is about 0.135 S/m (all genders, all subjects), only one of the displacements could clearly be considered negative. A few others may be somewhat negative as they are about one standard deviation below zero.

Figure 10:
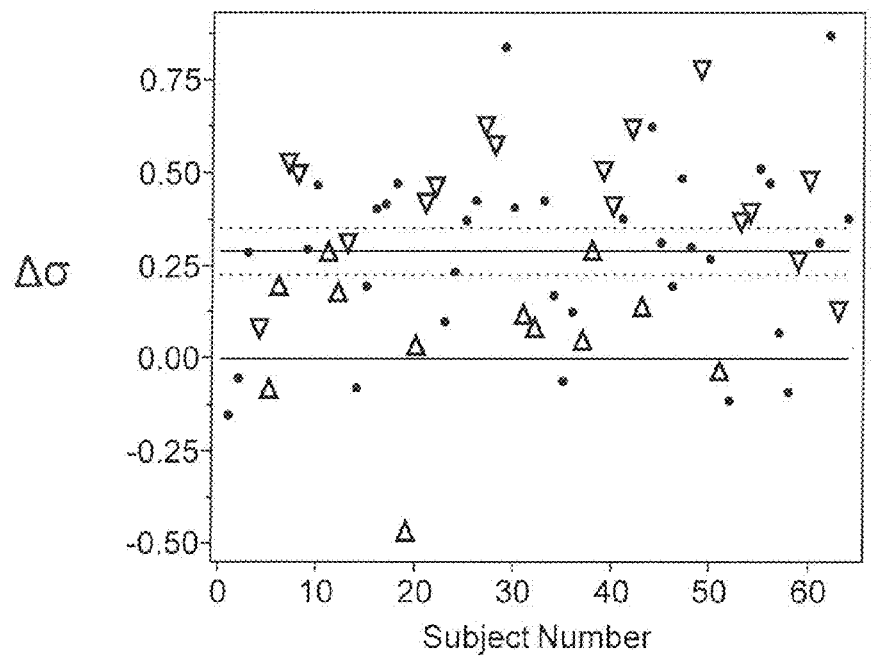

While there are several data points in FIG. 9 that show little or no change at all, most show a positive conductivity displacement. To investigate the origin of the spread of data, the plot is repeated in FIG. 10, with all those Clinical Study #1 male subjects who exhibited high blood pressure (in either arm) marked as upward directed triangles. Only men are included since only men participated in the Clinical Study #2. FIG. 10 shows the results. Upward triangles represent data collected from high systolic blood pressure subjects. Downward triangles represent data collected from subjects with diastolic blood pressure less than about 65 mm Hg.

FIG. 10 clearly shows raised systolic blood pressure is a key factor influencing the extent to which electrical conductivity rises (or does not rise) in response to elevation change. Note that not a single high blood pressure individual contributes to the pool of data located above the mean conductivity displacement. It is also clear that low diastolic blood pressure in the right arm contributes to a more dramatic upward response to elevation change. Low diastolic BP for purposes of either Clinical Study is defined to be less than about 65 mm Hg. Note that no subject identified as having low diastolic BP in the right arm exhibits a negative conductivity displacement $\Delta\sigma$. However, low or high blood pressure alone cannot be the only factors influencing elevation-related conductivity displacement $\Delta\sigma$.

Other parameters, such as extremity temperature (not measured) and height are also likely to play a role. The latter parameter would affect the amount of elevation change possible for subjects as well as any characteristic relaxation time for drainage (taller individuals would require more time to "drain").

The impact of blood pressure and temperature on storage of blood in the extremities and the adjustment in storage volume in response to a mechanical perturbation such as elevation change is a complex issue. Nevertheless, the behavior of FIGS. 9 and 10, even for those individuals with somewhat elevated blood pressure, is typical for a healthy study group. Those with lower diastolic blood pressure should exhibit a more notable increase in electrical conductivity in response to forearm elevation, while those with high systolic blood pressure should exhibit little or no rise.

In Clinical Study #2, the decision was made to reduce the time of elevation to 30 seconds, partly to avoid any discomfort to subjects, but also because separate measurements seemed to indicate that a shorter time would be acceptable. There was no initial decision on exam room temperature as the reduced temperature was only realized two days into Clinical Study #2 trial. Furthermore, forearm measurements were done at the proximal volar location rather than the mid volar location for the sake of measurement convenience. All three of these experimental alterations may have influenced the results of Clinical Study #2.

Figure 11:
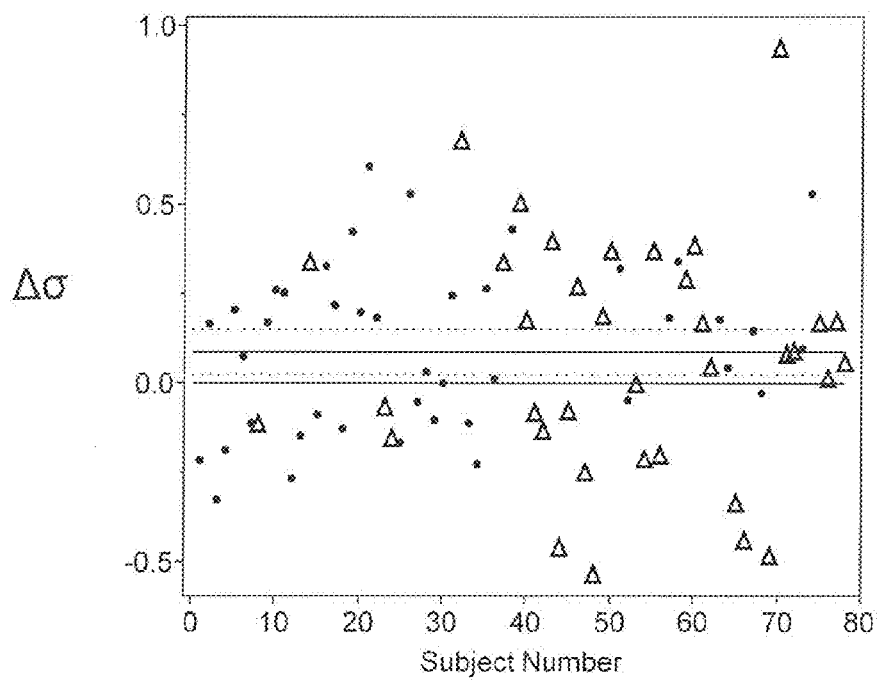

FIG. 11 shows electrical conductivity displacements at the right proximal volar forearm in response to elevation change for Clinical Study #2, after 30 seconds of elevation. Data are sorted first by smoking (1-48: nonsmokers; 49-78: smokers) and then by age (subjects of greatest age appear as #48 and #78 on the plot). Those with high right-arm systolic blood pressure are indicated with upward directed triangles. Only one subject (from risk group 1) had a right arm diastolic blood pressure less than 65 mm Hg (morning visit). His displacement during that visit was 0.22±0.06 S/m, but during his second visit, when diastolic BP was 70, conductivity displacement was negative, −0.128±0.06 S/m. Of the four subjects reporting a diabetic condition, three had high blood pressure, but otherwise did not form a particularly unique pattern in the figure—one displayed strongly negative displacements $\Delta\sigma$ for both visits, another had split readings with one clearly negative and the other positive, while the remaining two exhibited modestly positive conductivity displacements $\Delta\sigma$ for both visits.

Two features of FIG. 11 are abundantly evident: (1) high blood pressure does not necessarily lead to depressed conductivity displacement $\Delta\sigma$ as found in Clinical Study #1; and (2) negative conductivity displacements $\Delta\sigma$ are entirely feasible and statistically significant.

Addressing the issue of variability between FIG. 10 and FIG. 11, replication variability associated with conductivity measurements at the right proximal forearm is remarkably low (~2.8%), suggesting that data uncertainty is not an issue. Other possible issues include location and measurement duration—(1) proximal volar forearm in the Clinical Study #2 but mid volar forearm in Clinical Study #2; and (2) 30 second wait time in Clinical Study #2 as opposed to 60 second wait time in Clinical Study 31. Given that more than half of the measurements show a positive conductivity displacement $\Delta\sigma$, it seems unlikely that wait time is too short. Because conductivity at proximal and mid locations is highly correlated, it would also seem unlikely that choosing the proximal location rather than the mid location should make any notable difference. Therefore, the results of FIG. 11, with its apparent scatter, are what one would expect from a group of subjects that are for the most part experiencing some vascular health related issue.

Clearly, major negative conductivity displacements $\Delta\sigma$, and greater variability itself, occur mostly among those who are older and those who smoke (#49-#78). Comparing FIGS. 10 and 11, it seems reasonable to conclude that conductivity measurements are profoundly influenced by the state of vascular health. Determination of the state of vascular health via conductivity measurements, however, lies in proper collection and interpretation of data.

Clinical Study #2 also produced results in which the conductivity displacement $\Delta\sigma$ became negative. To address these results, the following guidelines and scenarios were proposed to be useful for interpretation of conductivity displacement $\Delta\sigma$ measurement in response to elevation change:

(1) As a result of increased limb elevation, unimpeded drainage of blood from the vascular circuit (from venules) occurs in a healthy vascular system. At the same time, less blood is supplied to capillaries through arterioles, leading to increased conductivity. This assumes no change in interstitial fluid volume.

(2) As a corollary to (1), less increase in conductivity or no increase at all should be expected when systolic blood pressure is greatly elevated; or, increased conductivity displacement $\Delta\sigma$ should be expected when diastolic blood pressure is low.

(3) In the event that only arterial blockage exists, the vascular bed still fills when a limb is not elevated, but with difficulty. When the limb is raised above the heart, arterial blockage may preclude normal filling so that increased conductivity in response to elevation is still observed, perhaps strongly so, and even when someone has high systolic blood pressure.

(4) If drainage from the venous side of the vascular circuit is greatly impaired due to blockage, though blockage is absent on the arterial side, then conductivity displacement is less noticeable or just nominal—assuming that interstitial fluid volume is unaffected by the elevation change.

(5) If blood volume remains essentially unchanged in response to elevation, but interstitial fluid enters blood or lymph vessels so that net drainage of interstitial fluid occurs to a significant degree, conductivity displacement should be negative, perhaps even sharply so. This may be an abnormal issue when blood vessels have become highly pervious and pressure differentials are such that interstitial fluids easily move into or out of capillaries, venules and lymph vessels. Or, when interstitial fluids cannot be replenished quickly enough to keep up with drainage, then strongly negative conductivity displacements may be expected.

(6) In general, with a variety of abnormal conditions present in the peripheral vascular system, any combination of the above scenarios could be present, leading to a complicated response of conductivity to mechanical perturbations, such as elevation change.

Given the wide range of possible scenarios that might arise, as described in the guidelines set forth above, the spread of data observed in FIG. 11 should perhaps not be surprising, but rather a strong indication of the complex array of vascular health issues that likely are present in the subjects participating in Clinical Study #2. The appearance of rather obvious patterns should only be expected in much more carefully controlled selections of participants, such as was the case in Clinical Study #1. Thus, many of the data points of FIG. 11 could be considered abnormal. In particular, invoking guideline (3) above, it may well be argued that everyone having high blood pressure and displaying high conductivity displacement $\Delta\sigma$ is suspect for some measure of arterial blockage. Furthermore, if the drainage issues described in guideline (5) are such that an arterial blockage prevents replacement of interstitial fluids at a rate sufficient to keep pace with drainage, then all subjects displaying a strongly negative conductivity displacement $\Delta\sigma$ are also suspect for disease.

For raised calf conductivity measurements, each subject was asked to lie flat on his back while positioned on the exam table. From that position, the nurse held either the right or left leg at an angle of about 60 degrees from horizontal. After 30 seconds, an electrical conductivity measurement was made. The data obtained indicates that calf electrical conductivity shows an exceptionally large conductivity displacement $\Delta\sigma$ in response to elevation. In every case, conductivity displacement is positive.

Even though conductivity measurements were not performed on elevated legs in Clinical Study #1, the guidelines proposed to explain trends for elevated right forearm conductivities from Clinical Study #1 were still applied to the interpretation of elevated calf data obtained in Clinical Study #2. General observations of data obtained during Clinical Study #2 include: a) essentially the same average upward conductivity displacement is found for either leg (about 1.25 S/m); b) all displacements are positive; c) the tallest member of the panel, by 6 inches, exhibited the least displacement of all those members of Group 1 (true for both legs); d) visit-to-visit variation can be extreme, (1.7 S/m; standard deviations for both points are about 0.075 S/m); e) 22 data points associated with high blood pressure subjects lie above the 95% confidence interval for the left calf, and 10 below, while 18 are above and 12 below the 95% confidence interval for the right calf.

Applying the guidelines set forth above, the data of Clinical Study #2 supports the conclusion that all those subjects with high blood pressure and exhibiting electrical conductivity displacements above the mean ought to have some level of arterial blockage. This assessment appears to be entirely consistent with a comparison of ratios of those deemed normal to abnormal across different categories. Working with left calf data, the normal:abnormal ratio for Risk Group 1 is 6.0 (6.0:1), while that for all smokers is 1.31 (1.31:1). Overall, left calf data gives a ratio equal to 2.25 (2.25:1). Interestingly, the same two subjects from Risk Group 1 who contribute to that group's "unhealthy" data for the left calf, also contribute to that group's unhealthy right calf data. Taking a look at those individuals who are older than 50 or smoke (subject number >35), examination of the data obtained reveals that the majority have both a high blood pressure condition and a conductivity displacement $\Delta\sigma$ exceeding the mean. This is definitely not true for subjects $\leq$50 years of age, and who don't smoke (subject number $\leq$35).

Analysis of the data obtained in Clinical Study #1 and Clinical Study #2 convincingly demonstrates that conductivity measurements are sensitive to the relative volumes of interstitial fluid and vascular tissue. Especially convincing is the effect of elevation on conductivity and the role that both systolic and diastolic blood pressure were shown to play on the extent of conductivity displacement in response to elevation change.

The normal expectation is that electrical conductivity ought to increase in response to increased elevation of an extremity. Because a limb is elevated, blood would be expected to exit venules more readily, but also encounter increased difficulty entering and filling capillaries via arterioles. Thus, electrical conductivity should increase in response to decreased volume fraction of the microvasculature. However, a decrease in conductivity is also possible in response to limb elevation, since this has been measured. Conductivity decrease will likely depend upon a wide variety of factors, which would include blockages that may be present at a variety of locations along the vascular circuit, and also the extent to which interstitial fluid itself may tend to drain out of a measurement site via the microvasculature. Drainage of interstitial fluid may be encouraged simply because of the pressure exerted at the site due to placement of the conductivity sensor firmly up against the skin. Alternatively, if a subject were to have a combination of significant venous blockage, elevated blood pressure, but ample opportunity for interstitial drainage via microvasculature, electrical conductivity could plummet in response to extremity elevation. This has been observed in higher risk subjects participating in Clinical Study #2.

Conductivity displacement measurements, in response to elevation changes, were shown to be especially effective at identifying those suspected with impaired vascular function. As demonstrated on healthy subjects in Clinical Study #1, individuals with high blood pressure should show conductivity displacements beneath the mean for the subject group. Subjects with a variety of risk factors in Clinical Study #2 were shown to be much more likely to violate this criterion than those in the low risk group. In particular, smokers with high blood pressure were highly likely to show conductivity displacements above the group mean. This could be the result of blockage on the arterial side of the vascular circuit, preventing the development of the normal level of blood volume one would expect from a high blood pressure individual.

When focusing just on un-elevated conductivity measurements of the upper extremities, the various analysis methods show that subjects having known health risks register electrical conductivity values well outside the norms established for subjects of much lower risk. In particular, smokers have much lower conductivities at sites on the upper extremities than they ought to have. As shown in Clinical Study #1 for all test sites without exception, conductivity at each body site declines with increased age. Thus, conductivity measurements show that smoking has the same effect as aging.

Another successful strategy for using electrical conductivity data involved the identification of conductivity outliers at all body locations, and determining their distribution over the various risk groups that were set up. Though outliers were progressively more likely to be found in risk groups one through four, fewer than expected were found in risk groups five and six. Since data outliers obtained from subjects who had both high blood pressure and an asymmetric blood pressure condition were distributed similarly, outlier distribution analysis might be effective in identifying those with that particular combination of blood pressure anomalies as well as its implications. For example, the importance of blood pressure disparities has been noted in the literature as a possible marker for peripheral vascular disease.

An unexpected result in Clinical Study #2 was the rather high electrical conductivities observed in the feet of most subjects. During measurement, the nurse noted that most subjects had cold feet while holding them in position for conductivity measurement. The examination room temperature was 68° F., 4° F. cooler than during Clinical Study #1. Though not planned at the outset, this glitch led to a result that provides further evidence that reduced blood volume in an extremity implies lowered vascular volume fractions, and higher conductivity as a result. A cooler environment is expected to cause some reduction in blood flow to the extremities, especially those farthest from the heart.

Ideally, electrical conductivity would be measured in an elevated limb as a function of time, leading to capture of transient behavior, perhaps over an interval lasting up to two minutes or more. Literature values for flow velocity in venules are about 1.0 cm/sec, while that in capillaries is reported to be about 0.5 cm/sec. If the distance that blood must move in order to see some elevation-related effect on electrical conductivity is about 30 cm, then a nominal "relaxation time" would range from about 30 to 60 seconds. Of course, the actual relaxation time will depend on a variety of factors, including temperature in the extremity and degree of muscle relaxation. Given that higher blood pressures tend to maintain blood volume and that pressures in Clinical Study #2 run considerably higher, 30 seconds may be too short—only one subject had a right arm diastolic pressure beneath 65 mm Hg. In the case of measurements at the calf while in the standing position, the problem of insufficient "settling" time is pronounced, since calf muscles had been relaxed for no more than about three seconds. In addition to the relaxation effects resulting from elevation changes and muscle tightness, there are also the relaxation processes associated with contact pressure between the conductivity sensor and the skin.

While the present subject matter has been described in detail with respect to specific exemplary embodiments and methods thereof, it will be appreciated that those skilled in the art, upon attaining an understanding of the foregoing may readily produce alterations to, variations of, and equivalents to such embodiments. Accordingly, the scope of the present invention is by way of example rather than by way of limitation, and the subject invention does not preclude inclusion of such modifications, variations and/or additions to the present subject matter as would be readily apparent to one of ordinary skill in the art.

What is claimed is:

1. A method of determining a vascular condition of an individual, comprising:
   performing a first conductivity measurement of an extremity of the individual at a first elevation;
   elevating the extremity of the individual to a second elevation;
   performing a second conductivity measurement of the extremity at the second elevation;
   comparing the first conductivity measurement and the second conductivity measurement to determine a conductivity displacement of the extremity responsive to the elevation change of the extremity.

2. The method of claim 1, wherein the first and second conductivity measurements are performed with a conductivity sensor comprising an induction coil.

3. The method of claim 2, wherein the conductivity sensor is configured to probe the extremity at a depth of up to about 15 mm below the skin of the individual.

4. The method of claim 3, wherein the induction coil comprises:
   a first conductive element that spirals outward to an external perimeter; and
   a second conductive element operably connected to the first conductive element, the second conductive element spiraling inward from the external perimeter staggered relative to the first conductive element.

5. The method of claim 1, wherein the first elevation is located substantially at or below the elevation of the heart of the individual and the second elevation is located above the heart of the individual.

6. The method of claim 1, wherein the extremity of the individual is an arm.

7. The method of claim 1, wherein the extremity of the individual is a leg.

8. The method of claim 1, wherein the method comprises:
   performing a blood pressure measurement of the extremity; and
   using the blood pressure measurement in conjunction with the conductivity displacement $\Delta\sigma$ to determine the vascular condition of the individual.

9. The method of claim 8, wherein the blood pressure measurement is the diastolic blood pressure of the individual.

10. The method of claim 8, wherein the blood pressure measurement is the systolic blood pressure of the individual.

11. The method of claim 1, wherein the method comprises using the conductivity displacement to determine if the individual has peripheral artery disease.

12. The method of claim 1, wherein the method comprises using the conductivity displacement to monitor patient warming.

13. The method of claim 1, wherein the method comprises using the conductivity displacement to monitor circulatory shock.

14. The method of claim 8, wherein the method comprises using the conductivity displacement to determine if the individual has venous or arterial blockage.

15. A method of assessing the health of a vascular system of an individual, the method comprising:
   performing a first conductivity measurement of the individual;
   subjecting the vascular system to a stimulus by subjecting the individual to vigorous exercise;
   subsequent to subjecting the vascular system to a stimulus, performing a second conductivity measurement of the individual; and comparing the first conductivity measurement and the second conductivity measurement to determine a conductivity displacement responsive to the stimulus.

16. The method of claim 15, wherein the first conductivity measurement is performed on an extremity of the individual at a first elevation and the second conductivity measurement is performed on the extremity at a second elevation.

17. The method of claim 16, wherein the first elevation is located substantially at or below the elevation of the heart of the individual and the second elevation may be located above the heart of the individual.

18. The method of claim 15, wherein the first and second conductivity measurements are performed with a conductivity sensor comprising an induction coil configured to probe the extremity at a depth of up to about 15 mm below the skin of the individual.

19. A method of assessing vascular health of an individual, comprising:
maintaining a conductivity sensor adjacent to the individual for a period of time;
performing a series of conductivity measurements of the individual, the series of conductivity measurements comprising a plurality of conductivity measurements taken over the period of time;
using the series of conductivity measurements to determine the transient behavior of the conductivity of the individual over the period of time; and
using the transient behavior of the conductivity to assess the vascular health of the individual;
wherein the conductivity measurements are performed with a conductivity sensor comprising an induction coil, the induction coil comprising a first conductive element that spirals outward to an external perimeter, and a second conductive element operably connected to the first conductive element, the second conductive element spiraling inward from the external perimeter staggered relative to the first conductive element.

20. The method of claim 1, wherein the series of conductivity measurements is performed on an extremity that is elevated above the heart of the individual.

21. The method of claim 19, wherein the method comprises performing each of the plurality of conductivity measurements in the series of conductivity measurements at regular predetermined time intervals for the period of time.

22. The method of claim 19, wherein the series of conductivity measurements are performed with a conductivity sensor comprising an induction coil configured to probe the specimen at a depth of up to about 15 mm below the skin of the individual.

23. The method of claim 19, wherein the method comprises monitoring the transient behavior of the conductivity of the extremity to determine if the individual has peripheral artery disease.

24. The method of claim 19, wherein the method comprises monitoring the transient behavior of the conductivity of the extremity to monitor patient warming.

25. The method of claim 19, wherein the method comprises monitoring the transient behavior of the conductivity of the extremity to monitor circulatory shock.

* * * * *

UNITED STATES PATENT AND TRADEMARK OFFICE
CERTIFICATE OF CORRECTION

PATENT NO. : 8,452,388 B2  Page 1 of 1
APPLICATION NO. : 12/464640
DATED : May 28, 2013
INVENTOR(S) : Feldkamp et al.

It is certified that error appears in the above-identified patent and that said Letters Patent is hereby corrected as shown below:

In the Claims

Column 24, Claim 20, line 7, after the word "claim", please delete "1" and insert --19--.

Signed and Sealed this
Twenty-ninth Day of July, 2014

Michelle K. Lee
*Deputy Director of the United States Patent and Trademark Office*